United States Patent
Vetterling et al.

(10) Patent No.: US 8,372,782 B2
(45) Date of Patent: Feb. 12, 2013

(54) IMAGING SYSTEM

(75) Inventors: William T. Vetterling, Lexington, MA (US); Chien Liu, Wayland, MA (US); Suhail Shabbir Saquib, Shrewsbury, MA (US); Brian David Busch, Sudbury, MA (US); Stephen Telfer, Arlington, MA (US)

(73) Assignee: Zink Imaging, Inc., Bedford, MA (US)

( * ) Notice: Subject to any disclaimer, the term of this patent is extended or adjusted under 35 U.S.C. 154(b) by 587 days.

(21) Appl. No.: 12/573,850

(22) Filed: Oct. 5, 2009

(65) Prior Publication Data
US 2010/0099556 A1 Apr. 22, 2010

Related U.S. Application Data

(63) Continuation-in-part of application No. 12/369,600, filed on Feb. 11, 2009, now abandoned, which is a continuation of application No. 11/656,267, filed on Jan. 22, 2007, now Pat. No. 7,504,360, which is a continuation of application No. 10/789,648, filed on Feb. 27, 2004, now Pat. No. 7,176,161.

(60) Provisional application No. 60/451,208, filed on Feb. 28, 2003.

(51) Int. Cl.
*B41M 5/337* (2006.01)
*B41M 5/34* (2006.01)

(52) U.S. Cl. .................. 503/204; 503/209; 503/226

(58) Field of Classification Search ............ None
See application file for complete search history.

(56) References Cited

U.S. PATENT DOCUMENTS

| | | |
|---|---|---|
| 2,417,897 A | 3/1947 | Adams |
| 3,488,705 A | 1/1970 | Fox et al. |
| 3,539,375 A | 11/1970 | Baum |
| 3,745,009 A | 7/1973 | Jenkins et al. |
| 3,832,212 A | 8/1974 | Jenkins et al. |
| 3,929,831 A | 12/1975 | Garner et al. |
| RE29,168 E | 4/1977 | Heseltine et al. |
| 4,097,288 A | 6/1978 | Lawton |
| 4,226,912 A | 10/1980 | Iwasaki et al. |
| 4,232,552 A | 11/1980 | Hof et al. |
| 4,243,052 A | 1/1981 | Bailey |
| 4,264,701 A | 4/1981 | Locatell, Jr. et al. |
| 4,380,629 A | 4/1983 | Yamashita et al. |
| 4,390,616 A | 6/1983 | Sato et al. |
| 4,401,717 A | 8/1983 | Ikeda et al. |
| 4,405,788 A | 9/1983 | Locatell, Jr. et al. |
| 4,415,633 A | 11/1983 | Nakamura et al. |

(Continued)

FOREIGN PATENT DOCUMENTS

| | | |
|---|---|---|
| DE | 96 668 C | 3/1898 |
| EP | 0107780 | 5/1984 |

(Continued)

OTHER PUBLICATIONS

PCT International Search Report—(PCT/US04/05986) Date of Mailing Sep. 15, 2004.

(Continued)

*Primary Examiner* — Bruce H Hess
(74) *Attorney, Agent, or Firm* — Foley & Lardner LLP; Michel Morency

(57) ABSTRACT

There are disclosed imaging members wherein a chemical compound in a crystalline form is converted, at least partially, and preferably substantially completely or completely, to an amorphous form that has intrinsically a different color from the crystalline form. Also described are imaging methods utilizing the imaging members. The conversion of the compound from the crystalline form to an amorphous form can be effected by laser exposure.

6 Claims, 6 Drawing Sheets

U.S. PATENT DOCUMENTS

| | | | |
|---|---|---|---|
| 4,436,920 A | 3/1984 | Sato et al. |
| 4,544,936 A | 10/1985 | Yokoi |
| 4,554,936 A | 11/1985 | Tingley |
| 4,602,263 A | 7/1986 | Borror et al. |
| 4,636,819 A | 1/1987 | Nagamoto et al. |
| 4,641,147 A | 2/1987 | Sakura et al. |
| 4,720,449 A | 1/1988 | Borror et al. |
| 4,728,633 A | 3/1988 | Satomura et al. |
| 4,803,148 A | 2/1989 | Harada et al. |
| 4,826,976 A | 5/1989 | Borror et al. |
| 5,177,262 A | 1/1993 | Taylor et al. |
| 5,256,619 A | 10/1993 | Yoshida et al. |
| 5,278,031 A | 1/1994 | Boggs et al. |
| 5,338,644 A | 8/1994 | Taylor et al. |
| 5,350,870 A | 9/1994 | Boggs et al. |
| 5,395,948 A | 3/1995 | Zink |
| 5,401,619 A | 3/1995 | Boggs et al. |
| 5,427,996 A | 6/1995 | Motoda et al. |
| 5,534,393 A | 7/1996 | Boggs et al. |
| 5,559,075 A | 9/1996 | Leenders et al. |
| 5,663,115 A | 9/1997 | Naito et al. |
| 5,667,943 A | 9/1997 | Boggs et al. |
| 5,869,420 A | 2/1999 | Naito et al. |
| 6,010,808 A | 1/2000 | Naito et al. |
| 6,054,246 A | 4/2000 | Bhatt et al. |
| 6,162,931 A | 12/2000 | Gee et al. |
| 6,165,706 A | 12/2000 | Fujiwara et al. |
| 6,229,055 B1 | 5/2001 | Klaubert et al. |
| 6,420,131 B1 | 7/2002 | Miller et al. |
| 6,537,410 B2 | 3/2003 | Arnost et al. |
| 6,801,233 B2 | 10/2004 | Bhatt et al. |
| 6,951,952 B2 | 10/2005 | Cheon et al. |
| 7,008,759 B2 | 3/2006 | Cheon et al. |
| 7,098,168 B2 | 8/2006 | Iwasaki et al. |
| 7,176,161 B2 * | 2/2007 | Chu et al. ............... 503/201 |
| 7,220,868 B2 | 5/2007 | Cheon et al. |
| 7,279,264 B2 | 10/2007 | Cheon et al. |
| 7,282,317 B2 | 10/2007 | Allen et al. |
| 7,408,563 B2 | 8/2008 | Busch et al. |
| 7,504,360 B2 * | 3/2009 | Chu et al. ............... 503/201 |
| 7,807,607 B2 | 10/2010 | Cheon et al. |
| 7,829,497 B2 | 11/2010 | Filosa et al. |
| 2004/0171817 A1 | 9/2004 | Allen et al. |
| 2004/0176248 A1 | 9/2004 | Chu et al. |
| 2004/0176617 A1 | 9/2004 | Cheon et al. |
| 2004/0191668 A1 | 9/2004 | Cheon et al. |
| 2004/0204317 A1 | 10/2004 | Cheon et al. |
| 2006/0232642 A1 | 10/2006 | Busch et al. |
| 2006/0276335 A1 | 12/2006 | Tsuboi et al. |
| 2006/0293185 A1 | 12/2006 | Filosa et al. |
| 2006/0293523 A1 | 12/2006 | Filosa et al. |
| 2007/0123421 A1 | 5/2007 | Chu et al. |
| 2007/0224552 A1 | 9/2007 | Cheon et al. |
| 2007/0238045 A1 | 10/2007 | Brocklin et al. |
| 2008/0058524 A1 | 3/2008 | Cheon et al. |
| 2008/0058525 A1 | 3/2008 | Allen et al. |
| 2008/0187866 A1 | 8/2008 | Cheon et al. |
| 2008/0238967 A1 | 10/2008 | Busch et al. |
| 2009/0137389 A1 | 5/2009 | Cheon et al. |
| 2010/0016154 A1 | 1/2010 | Chu et al. |
| 2010/0099556 A1 | 4/2010 | Vetterling et al. |

FOREIGN PATENT DOCUMENTS

| | | |
|---|---|---|
| EP | A-0 568 344 | 11/1993 |
| EP | A-0 591 106 | 4/1994 |
| EP | 0 576 015 | 6/1998 |
| EP | 0588 344 B1 | 3/2000 |
| EP | 1 234 681 | 8/2002 |
| EP | A-1 491 590 | 12/2004 |
| GB | 1298462 | 12/1972 |
| GB | A-2 031 600 | 4/1980 |
| GB | 2311 075 A | 9/1997 |
| JP | 49 023007 A | 3/1974 |
| JP | 56 027393 A | 3/1981 |
| JP | 58 038192 A | 3/1983 |
| JP | 59062666 | 4/1984 |
| JP | 62288828 | 12/1987 |
| JP | 04 016382 A | 1/1992 |
| JP | 04213368 | 8/1992 |
| JP | 05 255340 A | 10/1993 |
| JP | 06 103790 A | 4/1994 |
| JP | 07076587 | 3/1995 |
| JP | 07304972 | 11/1995 |
| JP | 2001-001645 | 1/2001 |
| WO | WO 02/96665 | 12/2002 |
| WO | WO-2004/078479 | 9/2004 |
| WO | WO 2004/078875 A | 9/2004 |

OTHER PUBLICATIONS

PCT International Search Report & Written Opinion—(PCT/US2010/051337) Date of Mailing Dec. 9, 2010.

Notice of Allowance, U.S. Appl.No. 11/433,808, Date of Mailing Jun. 25, 2010.

U.S. Appl. No. 12/750,539, filed Mar. 30, 2010, Cheon et al.

Masahiko et al., "New Thermo-Response Dyes: Coloration by the Claisen Rearrangement and Intromolecular Acid-Base Reaction", Angew. Chem. Int. Ed. Engl., 1992, vol. 31, pp. 204-205.

"Imaging Processes and Materials", Neblette's Eighth Edition, J. Sturge, V.Walworth, A. Shepp, Eds., Van Nostrand Reinhold, 1989, pp. 274-275.

Ian Fletcher and Rudolf Zink, "Sythesis and Properties of Phthalide-type Color Formers", in "Chemistry and Applications of Leuco Dyes", Ramaiah Muthyala, Ed., Plenum Press, New York, 1997, pp. 97-123.

PCT International Search Report (PCT/US06/18450) Date of Mailing Sep. 25, 2007.

PCT International Search Report (PCT/US06/18386) Date of Mailing Jun. 20, 2008.

EPO European Search Report—(06759686.6) Date of completion of search Feb. 6, 2009.

"Rhodamine dyes and related compounds", Zhurnal Organicheskoi Khimii, 1972, vol. 8, pp. 1726-1729, XP009111705.

"Bestimmung der Quantenausbeute der Rubinfluoreszenz bei Anregung durch Einstrahlung in eine blauen Absorptionslinien", Zeitschrift Fuer Physik, 1962, vol. 167, pp. 446-451, XP009111706. Compounds with RN 846606-85-1 and RN 879669-29-1 published in 1914.

Beilstein Institute for Organic Chemistry, Frankfurt-Main, Germany; (1988-2001); XP-002290704, pp. 1-4.

Beilstein Institute for Organic Chemistry, Frankfurt-Main, Germany; (1988-2001); XP-002290705, pp. 1-2.

Beilstein Institute for Organic Chemistry, Frankfurt-Main, Germany; (1988-2001); XP-002290706, pp. 1-2.

Beilstein Institute for Organic Chemistry, Frankfurt-Main, Germany; (1988-2001); XP-002290707, pp. 1-2.

Beilstein Institute for Organic Chemistry, Frankfurt-Main, Germany; (1988-2001); XP-002290708, pp. 1-2

Mizutani et al., "Hydrogen-bonding-based thermochromic phenol-amine complexes", *Journal of Physical Organic Chemistry*, (1998), 11:737-742.

Non-final Office Action (U.S. Appl. No. 11/433,810) dated Jul. 9, 2008.

Orban et al., "Formation of Hydrogen-bonded Complexes between Phenol and Some Heterocyclic Bases in Carbon Tetrachloride", *J. Chem. Soc. Perkin Trans. II* (1987), pp. 1815-1817.

PCT International Search Report—(PCTUS09/32443) Date of Mailing Mar. 3, 2009.

Savvin et al, "Mechanism of action of cationic surfactants in Organic reagent-metal ion-surfactant systems", (1978), 33(8)pp. 1473-1480.

Siegel et al., "Infrared study of the interaction between proton donors and 1,10-phenanthroline derivatives", *Spectrochimica Acta*, (1989), 45A:1297-1304.

Spencer et al., "Hydrogen Bond Equilibria of Phenol-Pyridine in Cyclohexane $CCl_4$, and Benzene Solvents", *J. Phys. Chem.* (1987), pp. 1673-1674.

Titov et al., "Equilibria of bisphenol complexation with pyridine in acetonitrile solutions", *Zhumal Obshchei Khimii* (1993), pp. 1869-1871. Journal written in Russian. English Abstract.

Yoshihiro Hatano, "The Chemistry of Fluoran Leuco Dyes", Ramaiah Muthyala, Ed., Plenum Press, New York, 1997, pp. 180-191.

IOFFE, et al., "Zhurnal Organicheskol Khimii", 1972, 8(8), pp. 1726-1729 (in Russia).

STN Search report and Abstract of IOFFE, et al., "Zhurnal Organicheskoi Khimii", 1972, 8(8), pp. 1726-1729.

PCT International Search Report—(PCTUS09/69464) Date of Mailing Mar. 30, 2010.

International Preliminary Report on Patentability for PCT International Application No. PCT/US2010/051337 DTD Apr. 11, 2012.

Communication Under Rule 71(3) EPC for European Patent Application No. 04 715 701.1 dated Oct. 21, 2011.

Extended European Search Report for EP 06770258.9 DTD Feb. 13, 2012.

Second Office Action for Chinese Patent Application No. 200680024340.1 dated Sep. 5, 2011 (English translation).

US Office Action on U.S. Appl. No. 12/869,226, DTD Mar. 1, 2012.

US Office Action on U.S. Appl. No. 12/940,709, DTD Oct. 27, 2011.

* cited by examiner

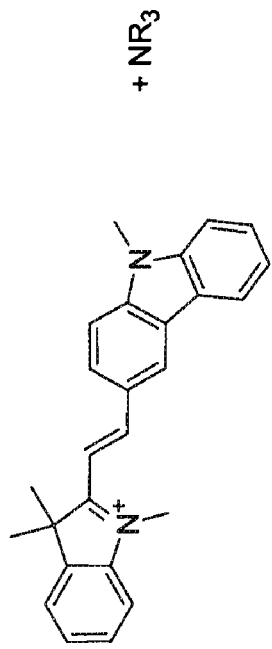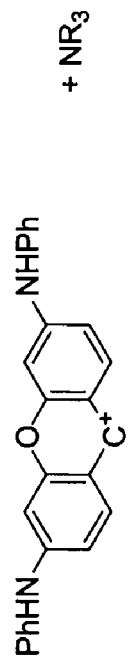 + NR$_3$
*Scheme 1*
Colored ⇌ Colorless
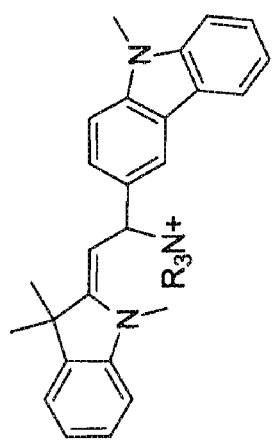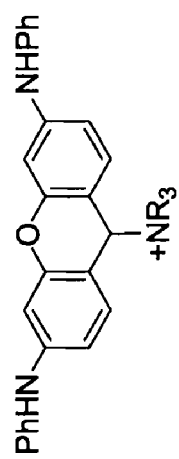 + NR$_3$
*Scheme 2*
Colored ⇌ Colorless
*Fig. 3*

IMAGING SYSTEM

REFERENCE TO RELATED APPLICATIONS

This application is a continuation-in-part of U.S. patent application Ser. No. 12/369,600, filed on Feb. 11, 2009, which is a continuation of U.S. patent application Ser. No. 11/656,267, filed on Jan. 22, 2007, now issued as U.S. Pat. No. 7,504,360, which is a continuation of U.S. patent application Ser. No. 10/789,648, filed on Feb. 27, 2004, now issued as U.S. Pat. No. 7,176,161, which claims benefit of prior provisional application Ser. No. 60/451,208, filed on Feb. 28, 2003, the contents of which are all hereby incorporated by reference in their entireties.

The present application is related to the following commonly owned United States patents and patent applications, the disclosures of all of which are hereby incorporated herein in their entirety:

U.S. Pat. No. 6,801,233 which describes and claims color-forming compositions for use in the present invention, U.S. Pat. No. 6,951,952 which describes and claims color-forming compositions for use in the present invention;

U.S. Pat. No. 7,008,759 which describes and claims color-forming compositions for use in the present invention;

U.S. Pat. No. 7,279,264 which describes and claims color-forming compositions for use in the present invention;

U.S. Pat. No. 7,388,686 which describes and claims methods for image stitching for use in the present invention;

U.S. Pat. No. 7,282,317 which describes and claims color-forming compositions for use in the present invention;

U.S. Pat. No. 7,408,563 which describes and claims imaging methods that include preheating for use in the present invention;

U.S. patent application Ser. No. 11/159,880, filed Jun. 23, 2005, entitled "Print Head Pulsing Techniques for Multicolor Printers";

U.S. patent application Ser. No. 11/400,734, filed Apr. 6, 2006, which describes and claims an imaging method for use in the present invention;

U.S. patent application Ser. No. 10/910,880, filed Aug. 4, 2004, which describes and claims a thermal response correction system for use in the present invention;

U.S. patent application Ser. No. 12/468,413, filed May 19, 2009, which describes and claims a thermal response correction system for use in the present invention;

U.S. patent application Ser. No. 12/022,955, filed on Jan. 30, 2008, which describes and claims an imaging method for use in the present invention; and U.S. patent application Ser. No. 12/462,421, filed on Aug. 3, 2009, which describes and claims an imaging member for use in the present invention.

FIELD OF THE INVENTION

This invention relates to imaging members, imaging methods for forming an image and a method for manufacturing a thermal imaging member and, more particularly, to imaging members and methods wherein formation of an image occurs when a chemical compound in a crystalline form is converted, at least partially, to an amorphous form, the amorphous form having intrinsically a different color from the crystalline form. The present invention also relates to multicolor direct thermal imaging wherein the source of heat is a laser or laser array.

BACKGROUND OF THE INVENTION

The development of thermal print heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed by heating. High sensitivity is important for maximum speed of printing, for maximizing the longevity of a thermal print head (when used), and for energy conservation in mobile, battery-powered printers. As described in more detail below, maximizing sensitivity while maintaining stability is more easily achieved if the temperature of coloration of a direct thermal medium is substantially independent of the heating time.

One method for printing a direct thermal imaging member uses a thermal print head in contact with a surface of a thermal imaging member. Thermal print heads address one line of the image at a time. For reasonable printing times, each line of the image is heated for about 50 milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Direct thermal imaging members that are exposed by lasers are known in the art. For example, U.S. Pat. Nos. 5,627,014, 5,153,169, 5,342,816 and 5,534,393 describe and claim imaging media comprising color-forming layers that contain a color-forming composition adapted to undergo a change of color upon increase in the temperature of the color-forming layer above a color-forming temperature for a color-forming time. Direct thermal imaging members described in these patents are exposed by lasers emitting in the near-infra-red (NIR) region of the electromagnetic spectrum (i.e., at wavelengths ranging from about 700 to about 1200 nm) and comprise three separate color-forming layers containing yellow, cyan and magenta thermal color-forming compositions. Each of these color-forming compositions comprises a color-forming compound which can produce the desired color and an infra-red absorber capable of absorbing infra-red radiation and thereby generating heat in the color-forming layer. The three color-forming layers use infra-red absorbers absorbing at differing wavelengths so that each color-forming layer can be imaged independently; for example, specific imaging media disclosed in these patents use infra-red absorbers having peak absorptions at approximately 792, 822 and 869 nm.

Many direct thermal imaging systems comprise a leuco (i.e., colorless) dye that is transformed into a colored compound by heat. Typically, a leuco dye does not absorb sufficient radiation from a laser emitting at a convenient wavelength to provide enough heat to effect the color change. For example, U.S. Pat. Nos. 4,602,263 and 4,826,976 (among many other examples) describe leuco dyes that absorb in the ultraviolet. At present, inexpensive ultraviolet lasers for imaging applications are not readily available. Moreover, it may be difficult to provide transparency to ultraviolet radiation in layers that are not intended to be heated by a laser. Visible wavelengths may be used, but in this case the absorber either needs to be bleached in a region of the final image that is intended to be white (i.e., reflecting as much as possible of incident visible light) or must be incorporated so as to absorb only a small fraction of the incident laser radiation. For these reasons, it is often preferred, as described above, to use lasers emitting in the NIR in conjunction with absorbers that absorb efficiently at these wavelengths but minimally at visible wavelengths. Such absorbers are described, for example, in U.S. Pat. Nos. 5,227,498, 5,227,499, 5,231,190, 5,262,549, 5,354,873, 5,405,976, 5,627,014, 5,656,750, 5,795,981, 5,919,950, 5,977,351 and 6,482,950. Even longer wavelengths in the infra-red, such as the output of gas lasers such as $CO_2$ lasers, may also be used.

It is not necessary that the infra-red absorber be incorporated into the color-forming layer itself, although this may be a preferred option. International Patent Application No. PCT/US87/03249, provides that an infra-red absorber may be provided in a layer adjacent the imaging layer to assist in converting infra-red radiation into heat.

The requirements for infra-red absorbers for use in thermal imaging systems are stringent. Since the sensitivity and the resolution of the image produced are often affected by the thickness of the layers in the heat-sensitive element (since the sensitivity of the system is inversely related to the mass of material required to be heated), it is necessary to provide a high degree of absorption of infra-red radiation within a thin layer, sometimes on the order of 1 micron in thickness. To produce this degree of absorption in a layer containing the other components required in thermal imaging systems, it is necessary that the infra-red absorber used have a high extinction coefficient, of the order of at least about 100,000 $Lmol^{-1}$ $cm^{-1}$, and a low molecular weight. In addition, the absorber should manifest its maximum absorption within the range of about 700-1200 nm so that it can conveniently be used with existing near infra-red lasers, and have minimal absorption at visible wavelengths. In the present state of technology, solid state diode lasers emitting at about 760 to 1200 nm provide the highest output per unit cost. YAG and other rare earth doped lasers emitting at about 1000-1200 nm are also useful in thermal imaging processes.

U.S. Pat. No. 5,534,393 provides that where imagewise heating is induced by converting actinic radiation to heat, the imaging medium may receive a non-imagewise general heating prior to or during the imaging step. Such heating may be achieved using a heating platen or heated drum or by employing an additional laser beam source or other appropriate means for heating the medium element while it is being exposed. This patent also provides for the addressing of different layers by controlling the depth of focus of a single laser (emitting at a single wavelength).

U.S. Pat. No. 7,314,704 describes imaging recording media that contain an absorber for laser radiation in conjunction with a colorless leuco dye, an activator and a fixer.

U.S. Patent Application No. 2008-0111877 describes an optical disc bearing a direct thermal imaging composition providing a full-color label that can be exposed by a laser.

Most chemical reactions speed up with increasing temperature. Therefore, the temperature required for coloration in the short heating time available from a thermal print head will normally be higher than the temperature needed to cause coloration during the long storage time. Reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be higher than the lamination temperature by as small a margin as possible, as would be the case for time-independent temperature of coloration.

Finally, the thermal imaging member may comprise more than one color-forming layer and be designed to be printed with a single thermal print-head, as described in the above-mentioned U.S. Pat. No. 6,801,233. In one embodiment of such a thermal imaging member, the topmost color-forming layer forms color in a relatively short time at a relatively high temperature, while the lower layer or layers form color in a relatively long time(s) at a relatively low temperature(s). An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, or may cause the color of a colored material to change, or may cause a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204-5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274-275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

Despite the many prior art examples of direct thermal imaging systems, therefore, there are none in which the temperature of image formation is substantially time-independent. In particular, there has not previously been described a method for producing an image in which a crystalline chemical compound is converted to a liquid, or amorphous, form, the liquid form having intrinsically a different color from the crystalline form.

SUMMARY OF THE INVENTION

It is therefore an object of this invention to provide a novel imaging method.

Another object of the invention is to provide a thermal imaging method wherein the temperature at which an image is formed is time independent.

It is another object to provide an imaging method wherein an image is formed by converting a solid chemical compound in the crystalline form, at least partially, to an amorphous form.

Still another object is to provide a multicolor thermal imaging method wherein an image in at least one color is formed by converting a solid chemical compound in the crystalline form at least partially to an amorphous form.

Yet another object of the invention is to provide novel imaging members.

Another object of the invention is to provide novel imaging members comprising a color-forming compound in a crystalline form and an associated absorber for incident NIR radiation.

According to one aspect of the invention there are provided imaging methods wherein a chemical compound in a crystalline form is converted, at least partially, and preferably substantially completely or completely, to an amorphous form, the amorphous form having intrinsically a different color from the crystalline form. The conversion to the amorphous form can be carried out by applying heat to the thermal imaging member by any of the techniques known in thermal imaging. In preferred embodiments, the energy required to form an image is provided by a laser.

In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline image-forming material to an amorphous form to form the image.

In another aspect of the invention there are provided novel thermal imaging members. The thermal imaging members of the invention generally comprise a substrate carrying at least one image-forming layer including a compound in the crystalline form, which can be converted, as described previously, at least partially to an amorphous form, the amorphous form having intrinsically a different color from the crystalline form. The thermal imaging member may be monochrome or multicolor and the temperature at which an image is formed in at least one of the image-forming layers is time independent.

The multicolor thermal imaging members of the invention may include at least one image-forming layer including a compound in the crystalline form, which can be converted, as described previously, at least partially to an amorphous form, the amorphous form having intrinsically a different color from the crystalline form and at least one image-forming layer including materials that form a color by a different mechanism.

In another aspect of the invention there is provided a method for manufacturing the thermal imaging members of the invention. Generally, the method includes the steps of forming a dispersion of the crystalline solid and optionally a binder, in a solvent in which the compound is insoluble or only sparingly soluble by any suitable method such as by grinding, attriting, etc. and forming a layer of the image-forming material on a substrate by any suitable method such as, for example, by coating the fluid onto the substrate using any of the techniques well-known in the coating art. These include slot, gravure, Mayer rod, roll, cascade, spray, and curtain coating techniques. The image-forming layer so formed is optionally overcoated with a protective layer or layers.

In a further aspect of the invention there is provided a substrate bearing at least a first color-forming layer, a first thermally-insulating interlayer, a second color-forming layer, a second thermally-insulating layer, and a third color-forming layer, wherein the first color-forming layer has a higher activation temperature than the second color-forming layer, and the second color-forming layer has a higher activation temperature than the third color-forming layer, including a radiation-absorbing material that is either within the first color-forming layer or located closer to the first color-forming layer than to any other color-forming layer.

BRIEF DESCRIPTION OF THE DRAWINGS

For a better understanding of the invention as well as other objects and advantages and further features thereof, reference is made to the following detailed description of various preferred embodiments thereof taken in conjunction with the accompanying drawings wherein:

FIG. 3 illustrates a chemical mechanism characteristic of materials which undergo the Type II mechanism;

DETAILED DESCRIPTION OF THE INVENTION

Compounds in the crystalline state commonly have properties, including color, that are very different from those of the same compounds in an amorphous form. In a crystal, a molecule is typically held in a single conformation (or, more rarely, in a small number of conformations) by the packing forces of the lattice. Likewise, if a molecule can exist in more than one interconverting isomeric forms, only one of such isomeric forms is commonly present in the crystalline state. In amorphous form or solution, on the other hand, the compound may explore its whole conformational and isomeric space, and only a small proportion of the population of individual molecules of the compound may at any one time exhibit the particular conformation or isomeric form adopted in the crystal. These phenomena are exploited in three similar ways in the compositions, imaging methods and imaging members of the present invention.

Figure 1:
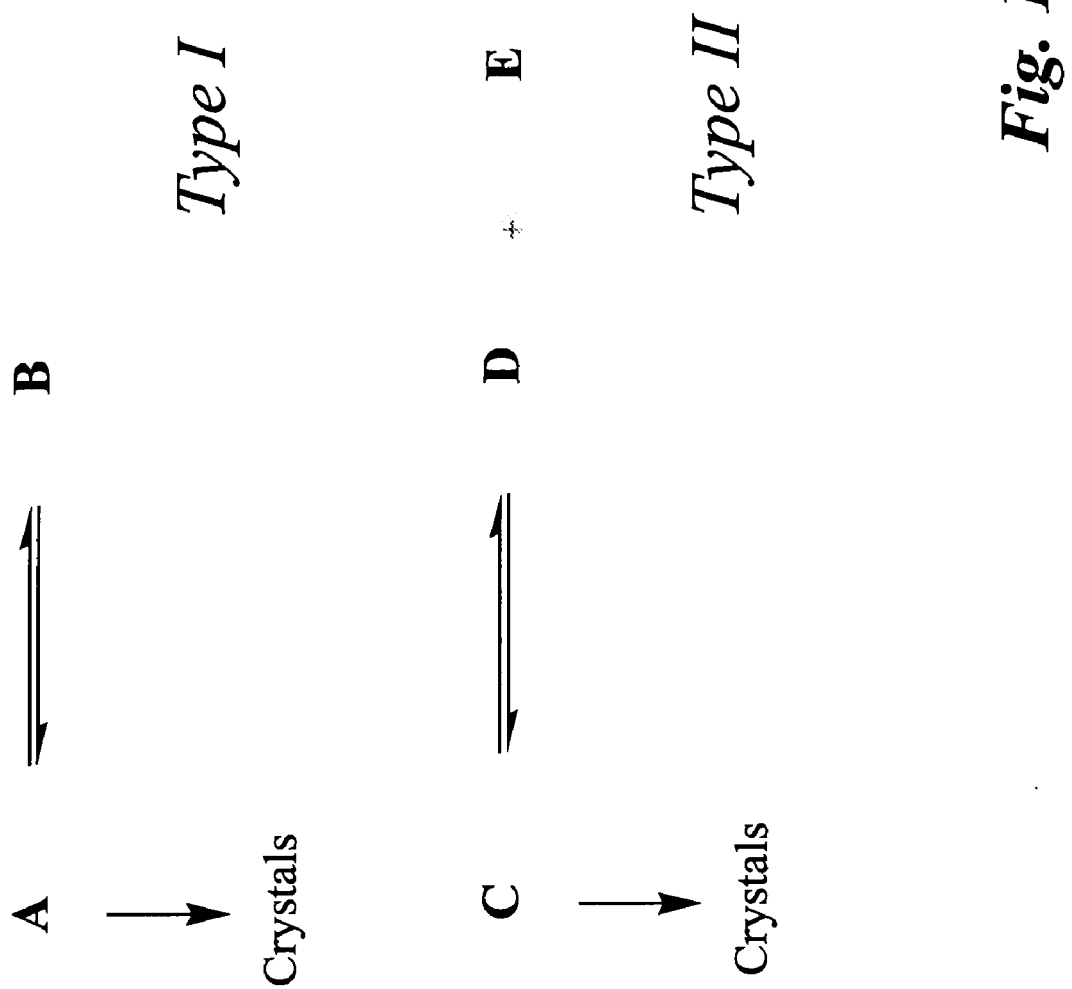
FIG. 1 illustrates two different chemical mechanisms, Types I and II, by which images can be formed according to the present invention.

Referring now to FIG. 1, there are seen two types of chemical equilibria that are exploited according to the present invention, designated Types I and II. The first type takes advantage of the fact that certain dye molecules exhibit tautomerism in solution (i.e., they exist as different, interconverting isomers at equilibrium). This is shown in FIG. 1, Type I, as the equilibrium between interconverting chemical entities A and B. Only two chemical species are shown in FIG. 1, Type I, but this is for the sake of simplicity only, and is not intended to limit the scope of invention in any way. The discussion provided herein applies equally to any number of interconverting tautomers. In the crystalline state, as described above, only one of the possible tautomeric forms will usually be present. Thus, crystallization of the mixture of A and B can produce crystals of pure A, or pure B, depending upon the conditions used.

Different tautomers may have different electronic structures from one another, and therefore different absorption of electromagnetic radiation. It is not unusual, therefore, for different tautomers to have different colors. The equilibrium distribution of tautomers will depend upon the polarity of the medium in which they are dissolved. Thus, a polar tautomer will be favored in a polar medium, while a less polar tautomer will be favored in a less polar medium. If a dye molecule exhibiting tautomerism can be crystallized into a single tautomeric form, the crystalline state will exhibit the color of that particular tautomer. If such a crystalline form is heated and converted to the liquid form or dissolved in a solvent, the tautomeric equilibrium will be re-established, so that at least some of the tautomer or tautomers not present in the crystal will be present, in relative amounts dependent upon the polarity of the molten state or solution. Since contributions from tautomers not present in the crystal will be seen, the color of the melt or solution is likely to be different from that of the crystal.

According to the invention, there have been identified molecules exhibiting tautomerism in which at least one tautomeric form is colorless, and at least another tautomeric form is colored. This is represented in FIG. 1, Type I, provided that molecule A is colorless, and molecule B is colored. Crystallization of the equilibrating mixture of A and B is carried out so as to produce colorless crystals of pure A. The solvent chosen to perform the crystallization will typically be one of such polarity (and other chemical properties, such as hydrogen-bonding ability) that A is favored, either in the equilibrium between A and B in solution, or in having lower solubility in the solvent than B. The choice of solvent is usually determined empirically for a particular mixture of tautomers.

Upon conversion of the pure crystalline A to an amorphous form, the equilibrium between tautomers A and B is re-established in the resulting amorphous (liquid) phase. The proportion of the amorphous material that is colored (i.e., the proportion that is in the B tautomeric form) may vary, but is preferably at least about 10%.

The colored and colorless tautomeric forms of the molecules of the present invention must meet certain criteria for image quality and permanence. The colorless form, which it is preferred be the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored, amorphous form should be stable also to the above mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For nonphotographic applications, however, it may be required that the colored form not be one of the subtractive primary colors, but rather a particular spot color (for example, orange, blue, etc.).

The thermal imaging members of the invention can be direct thermal imaging members wherein an image is formed in the member itself or they can be thermal transfer imaging members whereby image-forming material is transferred to an image-receiving member. The melting point of the molecules used in direct thermal imaging members of the present invention is preferably in the range of about 60° C. to about 300° C. Melting points lower than about 60° C. lead to direct thermal imaging members that are unstable to temperatures occasionally encountered during handling of the members before or after imaging, while melting temperatures above about 300° C. render the compounds difficult to colorize with a conventional thermal print head. It should be noted, however, that there are uses for certain novel compounds of the present invention that do not require the use of thermal print heads (for example, laser imaging).

The conversion of the crystalline form to an amorphous form upon heating or dissolving the crystalline compounds of the present invention may produce a material of high or low viscosity. Typically, amorphous materials with viscosities higher than $10^{12}$ Pa·s are referred to as glasses. It may be that melting of the crystalline form produces a free-flowing liquid that, upon cooling, becomes a glass. The temperature at which the viscosity reaches $10^{12}$ Pa·s upon cooling is referred to as the glass transition temperature, or Tg. In order to form an image having a desirable degree of stability, it is preferred that recrystallization of the liquid or amorphous form into the crystalline form not occur. It is more likely that recrystallization will be slow when the liquid or amorphous form is a glass, i.e., is at a temperature below its Tg. For this reason it is preferred that the Tg of the liquid or amorphous form of the compounds of the present invention be substantially above room temperature. Preferred Tg is about 50° C. or greater.

The multicolor thermal imaging members of the invention include those wherein all the color-forming layers are carried on the same side of a substrate as well as those wherein at least one color-forming layer is carried on a first side of a substrate and at least one color-forming layer is carried on a second side of the substrate.

Figure 2:
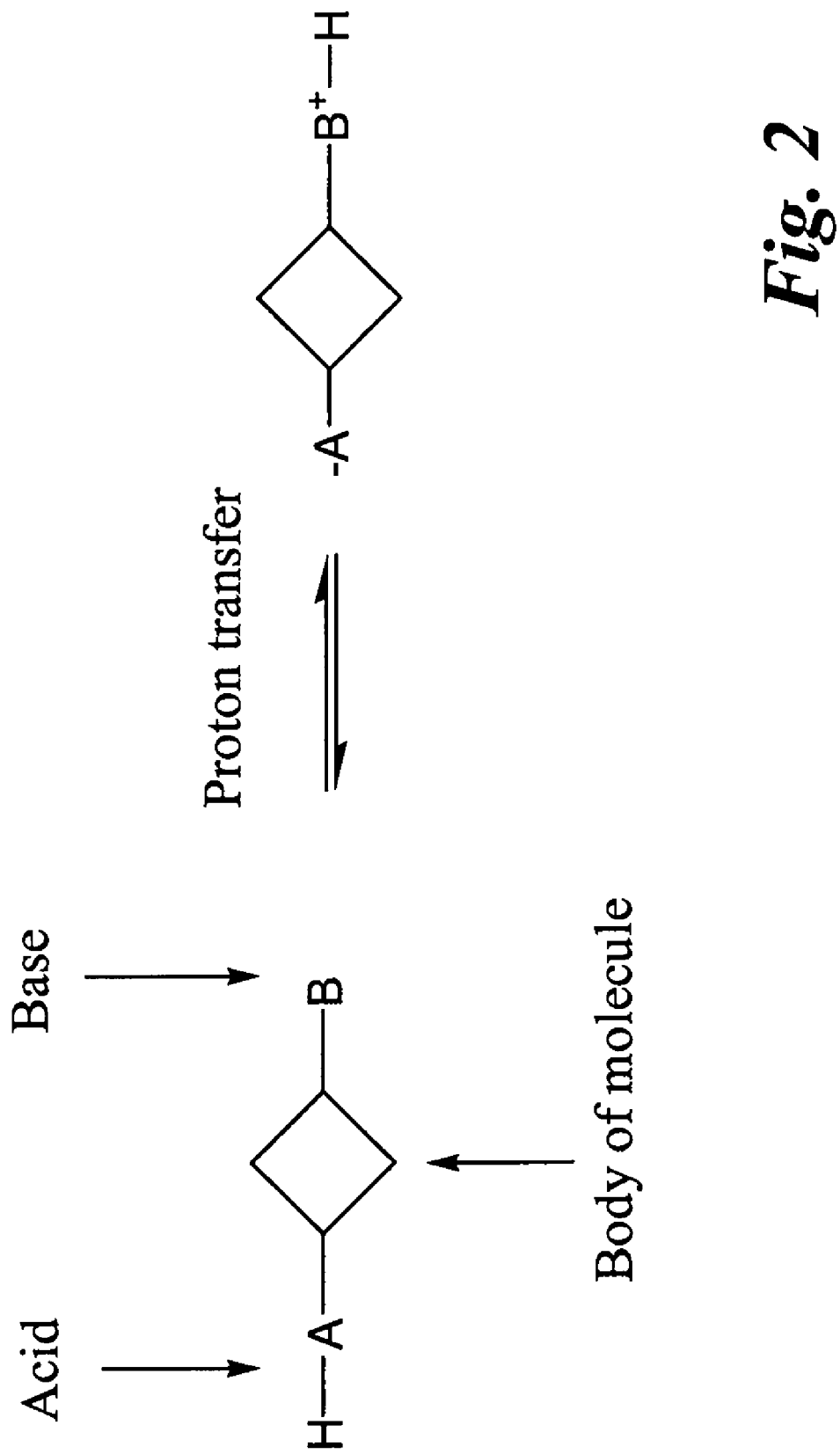
FIG. 2 illustrates a proton transfer equilibrium characteristic of materials which undergo the Type I mechanism shown in FIG. 1.

A preferred tautomeric equilibrium of the present invention involves proton transfer. As shown in FIG. 2, a molecule containing an acidic and a basic site can exist either in the protonated acid and unprotonated base tautomeric form, or in the unprotonated acid and protonated base form. These two forms can have different colors if either the acidic site or the basic site of the molecule constitute an indicator dye. Thus, the molecule might consist of a colorless, basic indicator dye (that becomes colored in the presence of an acid) covalently joined to an acid, or a colorless, acidic indicator dye (that becomes colored when deprotonated) covalently joined to a base. Of course, the molecule may also consist of a basic indicator dye covalently joined to an acidic indicator dye. The strengths of the acidic and the basic sites must be such that an equilibrium may be established that does not overwhelmingly favor one of the two tautomers under most conditions. This is most easily achieved if the acid and the base are weak. An especially preferred acidic grouping is a phenol, while the basic site may vary widely, commonly being an electronegative heteroatom such as oxygen or nitrogen.

Preferred examples of tautomeric molecules of Type I of the present invention include the following xanthene derivatives. Two tautomeric forms of the xanthene derivatives are shown (represented by formulae I and II), but this is not meant to exclude additional tautomeric forms of the molecule. It should be noted that some of the literature reports only one of the possible tautomers of xanthene molecules.

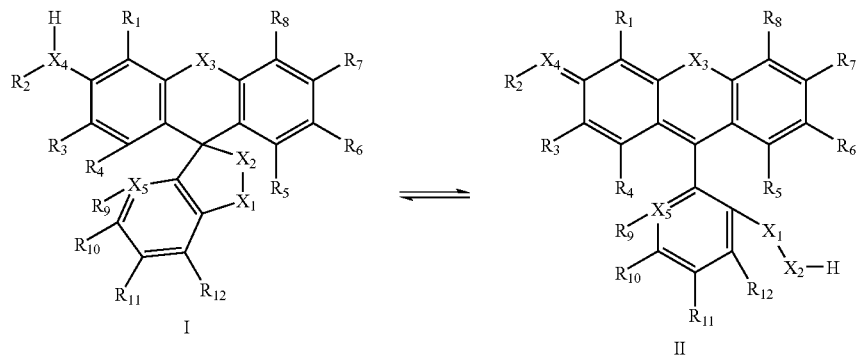

I                II

In these molecules $R_1$, $R_3$, $R_4$, $R_5$, $R_6$, and $R_8$ are each independently hydrogen, alkyl, aryl, halogen, or a substituted or unsubstituted oxygen, nitrogen or sulfur atom;

$R_2$ is hydrogen, alkyl, aryl, or is absent;

$R_7$ is substituted or unsubstituted oxygen, nitrogen, sulfur, or halogen;

$R_9$, $R_{10}$, $R_{11}$ and $R_{12}$ are each independently hydrogen, alkyl, aryl, halogen, nitro or substituted or a unsubstituted oxygen, nitrogen or sulfur atom, or absent;

$X_1$ is carbonyl, methylene, or sulfonyl;

$X_2$ is oxygen or nitrogen, substituted with hydrogen, alkyl, aryl, or nitrogen;

$X_3$ and $X_4$ are each independently oxygen, sulfur, or nitrogen; and $X_5$ is carbon or nitrogen.

In these compounds, the acidic grouping of formula I comprises the group $X_4$ bearing the hydrogen atom, and the basic site of formula I comprises the atom X2. Transfer of a proton from $X_4$ to $X_2$ gives a compound of formula II.

One preferred subgroup of xanthenes of formula I are fluorescein compounds, wherein $X_4$ is oxygen and $R_7$ is oxygen substituted with hydrogen, alkyl or aryl; and $X_1$ is carbonyl; $X_2$ is oxygen; and $X_3$ is oxygen.

Many fluorescein derivatives of the above subtype are known in the art. One tautomeric form (corresponding to formula I) of such compounds is colorless (absorbing in the ultraviolet region of the electromagnetic spectrum), whereas a second tautomeric form (corresponding to formula II) is often yellow in color. Fluorescein itself is the compound of formula I, in which $R_2$ is absent, $R_7$ is a hydroxyl group, $R_1$, $R_3$, $R_4$, $R_5$, $R_6$, $R_8$, $R_9$, $R_{10}$, $R_{11}$ and $R_{12}$ are each hydrogen atoms, $X_1$ is carbonyl, $X_2$, $X_3$ and $X_4$ are each oxygen and $X_5$ is carbon. It has been found that there are difficulties with many of these prior art compounds. Fluorescein itself is difficult to crystallize in a colorless form and in the amorphous form exhibits complex equilibria including several, differently colored species. A simplification may be made if $R_7$ is an ether grouping. Thus, the previously known compound benzyl fluorescein, in which the substituents are as described above for fluorescein itself except that $R_7$ is a benzyloxy group, is readily crystallized into a colorless form. The amorphous form of benzyl fluorescein has a yellow color.

Benzyl fluorescein has the disadvantage that only a small proportion of the amorphous form (about 4%) is colored (i.e., about 96% of the amorphous form is in the tautomeric form corresponding to formula I, and about 4% in the structure corresponding to formula II). It has been found that much higher proportions of the colored tautomer in the amorphous form may be obtained when at least two of $R_1$, $R_3$, $R_6$ and $R_8$ in formula I comprise an alkyl substituent, as described in more detail in Example 1 below.

Especially preferred fluorescein derivatives of the present invention are derivatives of formula I in which at least two of $R_1$, $R_3$, $R_6$ and $R_8$ comprise an alkyl group having between one and about twelve carbon atoms, which may be branched or linear, and which may comprise aryl or heteroatomic substituents, $R_2$ is absent, $R_4$, $R_5$, $R_9$, $R_{10}$, $R_{11}$ and $R_{12}$ are each hydrogen, $R_7$ is an ether grouping, $X_1$ is a carbonyl group, $X_2$, $X_3$ and $X_4$ are each oxygen and $X_5$ is carbon.

Specific preferred compounds of formula I are those in which $R_2$ is absent, $R_4$, $R_5$, $R_9$, $R_{10}$, $R_{11}$ and $R_{12}$ are each hydrogen, $X_1$ is carbonyl, $X_2$, $X_3$ and $X_4$ are each oxygen, $X_5$ is carbon, and the other substituents are as follows:

Compound F-1: $R_1$ and $R_8$ are each hydrogen, $R_3$ and $R_6$ are each n-hexyl and $R_7$ is benzyloxy;

Compound F-2: $R_1$ and $R_8$ are each hydrogen, $R_3$ and $R_6$ are each n-hexyl and $R_7$ is ethoxy;

Compound F-3: $R_1$ and $R_8$ are each hydrogen, $R_3$ and $R_6$ are each ethyl and $R_7$ is benzyloxy;

Compound F-4: $R_1$ and $R_8$ are each hydrogen, $R_3$ and $R_6$ are each n-hexyl and $R_7$ is ethoxy;

Compound F-5: $R_1$ and $R_8$ are each methyl, $R_3$ and $R_6$ are each hydrogen and $R_7$ is benzyloxy;

Compound F-6: $R_1$ and $R_8$ are each methyl, $R_3$ and $R_6$ are each hydrogen and $R_7$ is 2-methoxyethoxy;

Compound F-7: $R_1$ and $R_8$ are each hydrogen, $R_3$ and $R_6$ are each ethyl and $R_7$ is 3-methylbut-1-oxy;

Compound F-8: $R_1$ and $R_8$ are each hydrogen, $R_3$ and $R_6$ are each ethyl and $R_7$ is 2-methylbenzyloxy;

Compound F-9: $R_1$ and $R_8$ are each hydrogen, $R_3$ and $R_6$ are each ethyl and $R_7$ is 3-methylbenzyloxy;

Compound F-10: $R_1$ and $R_8$ are each hydrogen, $R_3$ and $R_6$ are each benzyl and $R_7$ is benzyloxy;

Compound F-11: $R_1$ and $R_8$ are each hydrogen, $R_3$ and $R_6$ are each propyl, and $R_7$ is benzyloxy; and Compound F-12: $R_1$ and $R_8$ are each hydrogen, $R_3$ and $R_6$ are each benzyl and $R_7$ is 3-methylbut-1-oxy.

A second preferred subgroup of xanthenes of formula I are rhodol-type compounds, wherein $X_4$ is oxygen, $R_2$ is absent and $R_7$ is nitrogen bearing two substituents each of which may independently be hydrogen, alkyl or aryl; $X_1$ is carbonyl; and $X_2$, $X_3$ and $X_4$ are each oxygen.

Preferred compounds of the rhodol type are those in which $R_1$ is hydrogen, halogen, or alkyl; $R_2$ is absent; $R_3$ is an electron-withdrawing substituent such as halogen, sulfonyl or nitro; $R_7$ is nitrogen bearing at least one aryl substituent; $R_4$, $R_5$, $R_6$, $R_8$, $R_9$, $R_{10}$, $R_{11}$ and $R_{12}$ are each hydrogen; $X_1$ is carbonyl; $X_2$, $X_3$ and $X_4$ are each oxygen; and X5 is carbon. It has been found that rhodol-type compounds can afford good magenta (green-absorbing) chromophores provided that R3 is an electron-withdrawing substituent such as a halogen, sulfonyl or nitro and $R_7$ is nitrogen bearing at least one aryl substituent. Absent the electron-withdrawing substituent at $R_3$, or the aryl substituent on the nitrogen atom at $R_7$, the wavelength of absorption is shorter, and the colored tautomer of the molecule exhibits a red, rather than a magenta, color.

Specific preferred rhodol-type compounds of formula I are those in which $R_2$ is absent; $R_4$, $R_5$, $R_6$, $R_8$, $R_9$, $R_{10}$, $R_{11}$ and $R_{12}$ are each hydrogen; $X_1$ is carbonyl; $X_2$, $X_3$ and $X_4$ are each oxygen; $X_5$ is carbon; and the other substituents are as follows:

Compound Rh-1: $R_1$ is hydrogen, $R_3$ is bromine and $R_7$ is phenylamino;

Compound Rh-2: $R_1$ is hydrogen, $R_3$ is bromine and $R_7$ is N-ethyl-N-phenylamino;

Compound Rh-3: $R_1$ is hydrogen, $R_3$ is bromine and $R_7$ is N-butyl-N-phenylamino;

Compound Rh-4: $R_1$ is hydrogen, $R_3$ is bromine and $R_7$ is N-hexyl-N-phenylamino;

Compound Rh-5: $R_1$ is hydrogen, $R_3$ is bromine and $R_7$ is N-benzyl-N-phenylamino;

Compound Rh-6: $R_1$ is hydrogen, $R_3$ is bromine and $R_7$ is N,N-diphenylamino;

Compound Rh-7: $R_1$ is methyl, $R_3$ is bromine and $R_7$ is N-hexyl-N-phenylamino;

Compound Rh-8: $R_1$ is hydrogen, $R_3$ is hydrogen and $R_7$ is N-indolinyl; and Compound Rh-9: $R_1$ is hydrogen, $R_3$ is bromine and $R_7$ is N-hexadecyl-N-phenylamino.

A third preferred subgroup of xanthenes of formula I are rhodamine-type compounds, in which $R_1$, $R_3$, $R_4$, $R_5$, $R_6$, $R_8$, $R_9$, $R_{10}$, $R_{11}$ and $R_{12}$ are each hydrogen, alkyl, aryl or halogen, $R_2$ is hydrogen, alkyl or aryl and $R_7$ is nitrogen bearing two substituents each of which independently may be hydrogen, alkyl or aryl, or oxygen bearing an alkyl or aryl substituent; $X_1$ is carbonyl; $X_2$ is oxygen; $X_3$ is oxygen; $X_4$ is nitrogen; and $X_5$ is carbon.

Specific preferred rhodamine-type compounds of formula I are those in which $R_1$, $R_3$, $R_4$, $R_5$, $R_6$, $R_8$, $R_9$, $R_{10}$, $R_{11}$ and $R_{12}$ are each hydrogen; $X_1$ is carbonyl; $X_2$ and $X_3$ are each oxygen; $X_4$ is nitrogen; $X_5$ is carbon; and the other substituents are as follows:

Compound R-1: $R_2$ is phenyl and $R_7$ is phenylamino;

Compound R-2: $R_2$ is 2-methylphenyl and $R_7$ is 2-methylphenylamino;

Compound R-3: $R_2$ is 2-ethylphenyl and $R_7$ is 2-ethylphenylamino;

Compound R-4: $R_2$ is 2,4,6-trimethylphenyl and $R_7$ is 2,4,6-trimethylphenylamino;

Compound R-5: $R_2$ is 2-chlorophenyl and $R_7$ is 2-chlorophenylamino.

Another specific preferred rhodamine-type compound of formula I is Compound R-6, in which $R_1$, $R_3$, $R_4$, $R_5$, $R_6$, and $R_8$ are each hydrogen, $R_2$ is a 2-methyl-4-octadecyloxyphenyl group, $R_7$ is an N-indolinyl group, $R_9$, $R_{10}$, $R_{11}$ and $R_{12}$ are each fluorine, $X_1$ is carbonyl, $X_2$ and $X_3$ are each oxygen, $X_4$ is nitrogen, and $X_5$ is carbon.

Two problems commonly occur in designing molecules for use according to the mechanism of Type I. Firstly, it may turn out to be impossible to crystallize the colorless tautomeric form of the molecule. For example, many of the rhodol-type compounds described above cannot readily be crystallized in a colorless form. Secondly, the colorless form may be able to be crystallized, but may exhibit a non-ideal melting point. To change the melting point would require complete redesign of the molecule, a long and tedious process. However, as described in U.S. Pat. No. 4,097,288, it is well known that certain phenolic or amino compounds readily form co-crystals with hydrogen-bonding acceptors or donors. Such hydrogen-bonding acceptors or donors are hereinafter referred to as "complexing agents". A co-crystal of a given molecule of the present invention in conjunction with a hydrogen-bonding complexing agent does not necessarily have the same melting point as either the complexing agent or the molecule of the present invention on its own.

As mentioned above, in each of the preferred types of formula I, atom $X_4$ bears a hydrogen substituent. This hydrogen atom, besides being the internal acid used to produce the colored tautomeric form of the molecule, is also available to be complexed by a hydrogen-bonding acceptor. Complexation, as described above, not only may enable crystallization of the colorless tautomeric form of the molecule in cases where this would otherwise be difficult to achieve, but may also allow control of the melting point. Preferred complexing agents are amino compounds, especially heterocyclic materials such as pyridines. Specific preferred complexing agents include phenanthroline, 2,9-dimethylphenanthroline, 4,5,6,7-tetramethylphenanthroline, methyl picolinate, ethyl picolinate, pyrazine, 4,4'-bispyridine, 2,2'-bispyridine, terephthalamides such as N,N,N',N'-tetramethylterephalamide and the corresponding tetrabutyl derivative, and cyclic oxalamides such as 1,4-dimethyl-2,3-dioxopiperazine. Example 4 below illustrates the effect of complexation to crystallize the colorless tautomeric form of rhodol-type compounds used in the present invention and to tailor the melting point of these and other molecules of the present invention.

The present invention is not limited to compounds that exist in different tautomeric forms. In a second embodiment of the invention, illustrated in FIG. 1, Type II, the equilibrium established is between a colorless adduct, shown as C, and its two constituents, shown as D and E. D is a colored dye, while E is a colorless molecule that can add to D and render it colorless. Typically, D is a cationic dye (an electrophile) and E is a nucleophile. During crystallization of C, the concentration of E may be made sufficiently high (and much higher than that of D) that very little of D is present. When C is melted, however, the concentration of D and E will be the same. The position of the equilibrium may thus be different in the amorphous form resulting from melting of C than it was in the solution from which C was crystallized in the first place. FIG. 3 shows two examples of equilibria that can be used for Type II of the present invention. Scheme 1 of FIG. 3 shows the equilibrium between a hemicyanine dye and a colorless adduct formed by addition of a tertiary amine. Scheme 2 shows a similar equilibrium established between a xanthene dye and a tertiary amine. A wide variety of nucleophilic molecules may be used to establish equilibria such as those shown in FIG. 3, but it is preferred that the adduct formed between the dye and the nucleophile have the same charge as the final dye. If this is not the case, for example if the adduct is neutral but the dye is positively charged, in order to maintain charge balance the nucleophile in the dissociated state must be negatively charged. In this case, it is likely that the nucleophile will remain closely associated with the dye due to electrostatic attraction. The adduct and the dye will both be positively charged if the dye is positively charged and the nucleophile is a tertiary amine, a tertiary phosphine, or a thioether, for example.

To form a direct thermal imaging system, the crystalline, colorless form of the compound of Types I or II described above is made into a dispersion in a solvent in which the compound is insoluble or only sparingly soluble, by any of the methods known in the art for forming dispersions. Such methods include grinding, attriting, etc. The particular solvent chosen will depend upon the particular crystalline material. Solvents that may be used include water, organic solvents such as hydrocarbons, esters, alcohols, ketones, nitriles, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrollidone) and cellulose derivatives, water-dispersed latexes such as styrene/butadiene or poly (urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art. These include slot, gravure, Mayer rod, roll, cascade, spray, and curtain coating techniques. The image-forming layer so formed is optionally overcoated with a protective layer or layers.

Where materials of the present invention are used to prepare an imaging medium of the type described in U.S. Pat. No. 6,801,233 the process described above is followed for each of the imaging layers. Successive layers may be coated sequentially, in tandem, or in a combination of sequential and tandem coatings.

EXAMPLES

The invention will now be described further in detail with respect to specific embodiments by way of examples, it being understood that these are intended to be illustrative only and the invention is not limited to the materials, amounts, procedures and process parameters, etc. recited therein. All parts and percentages recited are by weight unless otherwise specified.

Example 1

This example describes the preparation and properties of novel fluorescein derivatives of formula I.

A. Novel fluorescein derivatives were prepared in the following general manner (exemplified by the preparation of Compound F-11).

Preparation of 4-propyl-1,3-dihydroxybenzene. i. 1,3-Dihydroxy-4-propanoylbenzene (10 g; 60.2 mmol) and trifluoroacetic acid (10 eq., 0.6 mol; 68.4 g) were stirred at room temperature until all the material was dissolved. To the resultant solution there was added triethylsilane (2.5 eq., 0.15 mol; 17.5 g) slowly at room temperature. After the addition, the reaction mixture was stirred with heating at 75° C. for 4 hours. The mixture was cooled to room temperature, quenched into water and extracted with dichloromethane to give two layers of oil product. The upper layer (excess triethylsilane) was decanted off and to the residual oil product there was added a mixture of hexane and dichloromethane (ca. 7:3 ratio) with heating to give a solid product. The product (7.3 g; 80% yield), whose structure was confirmed by 1H NMR and Electrospray mass spectrometry (ES MS) was used for the next step without further purification.

ii. Preparation of 2,7-dipropylfluorescein.

To a mixture of 4-propyl-1,3-dihydroxybenzene (6.0 g; 40 mmol, prepared as described in (i) above) and phthalic anhydride (20 mmol; 3.0 g) there was added 73% (w/w) concentrated sulfuric acid at room temperature and the mixture was then stirred with heating at 150° C. for 3 hours. After cooling, the mixture was poured into water (200 mL) with stirring in the beaker, filtered, and washed with water several times to give yellow product with a quantitative yield. The structure of the product was confirmed by 1H NMR and ES MS.

iii. Preparation of compound F-11.

2,7-Dipropylfluorescein (3 g; 7.2 mmol, prepared as described in (ii) above) and anhydrous potassium carbonate (4 eq., 28.8 mmol) were dispersed in dimethylformamide (DMF, 35 mL) at room temperature and the mixture was then stirred with heating at 100° C. until reddish clear solution appeared. To the resultant solution was added benzyl bromide (4 eq., 28.8 mmol; 4.9 g) dissolved in DMF (5 mL) slowly for 10 min. After the addition had been completed the mixture was further stirred at 100° C. for another 3 hours. After cooling the mixture to room temperature it was poured into water (400 mL) to give a precipitate. The crude product (monoether, monoester) was hydrolyzed without further purification. The monoether monoester product was dissolved in a mixture of acetone (60 mL) and water (20 mL) and to this solution there was added aqueous sodium hydroxide (4 eq., 28.8 mmol; 1.2 g; 12 mL a 10% aqueous solution). The mixture was stirred at room temperature overnight. After evaporation of acetone the mixture was diluted with water (200 mL) and filtered. The filtrate was neutralized with dilute hydrochloric acid to give pale yellow precipitate. The crude product was purified by silica gel column chromatography (eluted with 3% methanol in dichloromethane) followed by recrystallization from a mixture of hexane and acetone to give colorless crystals (1.75 g, 48% yield, mp 202-203° C.)

B. The fluorescein derivatives so prepared, having structures described hereinabove, exhibited the following properties:

| Compound | Color of melt | Melting point (° C.) | Melting Range (° C.) |
|---|---|---|---|
| F-1 | Yellow | 111* | — |
| F-2 | Yellow | 225* | — |
| F-3 | Yellow | 230* | — |
| F-4 | Yellow | 107 | 7.2 |
| F-5 | Orange | 220* | — |
| F-6 | Orange | 251 | 5.4 |
| F-7 | Yellow | 194 | 5.0 |
| F-8 | Yellow | 115* | — |
| F-9 | Yellow | 160* | — |
| F-10 | Yellow | 219 | 4.6 |
| F-11 | Yellow | 210 | 5.3 |
| F-12 | Yellow | 207 | 4.6 |

Unless indicated by (*), melting points were determined by differential scanning calorimetry (DSC) at a temperature ramp rate of 4° C./min.
*Indicates that melting points were obtained using a capillary melting point apparatus.

Example 2

This example describes the preparation of novel rhodol-type derivatives of the invention. Derivatives Rh-1-Rh-7 were prepared in the following general manner (exemplified by Rh-7).

ia. Preparation of 2-(5-bromo-2,4-dihydroxybenzoyl)benzoic acid (Starting Material for Rh-1-Rh-6 and Rh-9).

Aluminum chloride (8.48 g, 64 mmol) was added to a stirring suspension of phthalic anhydride (2.36 g, 16 mmol) in tetrachloroethane (40 mL) under nitrogen. Nitromethane (6 mL) was added to dissolve the reactants. 4-Bromoresorcinol (3 g, 16 mmol) was added and the mixture continued to stir under nitrogen. The reaction was monitored by high performance liquid chromatography (HPLC) over a period of 2 hours. It was observed that the reaction had ceased within the first 30 minutes, with starting materials remaining. The solution was diluted with ethyl acetate (~150 mL) and washed with 1M hydrochloric acid (2×100 mL). The product was extracted from the organic layer into a saturated solution of sodium bicarbonate in water (200 mL). The basic aqueous phase was acidified with 3M hydrochloric acid to a pH of 5. The product was extracted from the aqueous phase into ethyl acetate (150 mL), washed with brine (2×100 mL), dried over magnesium sulfate and concentrated to give an orange oil which solidified upon standing for about 10 minutes. The solid was slurried in dichloromethane (20 mL) and filtered to give a mixture of the desired product and phthalic acid. Slurrying in water (20 mL) followed by filtration gave the desired product as a beige powder (1.72 g, 5.1 mmol, 32% yield).

ib. Alternative Preparation, Illustrated for 2-(5-bromo-2,4-dihydroxy-3-methylbenzoyl)benzoic acid (Starting Material for Rh-7).

Step 1: Aluminum chloride (21.4 g, 161 mmol) was added to a stirring suspension of phthalic anhydride (6 g, 40 mmol) in tetrachloroethane (200 mL) under nitrogen. 1,3-Dihydroxy-2-methylbenzene (5 g, 40 mmol) was added and the mixture quickly thickened. After the precipitates were broken up with a spatula the reaction continued for 1 hour. The solution was diluted with ethyl acetate (~600 mL) and washed with 1M hydrochloric acid (2×200 mL). The product was extracted from the organic layer into a saturated solution of sodium bicarbonate in water (600 mL). The basic aqueous phase was acidified with 3M hydrochloric acid to a pH of 5. The product was extracted from the aqueous phase into ethyl acetate (400 mL), washed with brine (2×100 mL), dried over magnesium sulfate and concentrated to give a brownish solid. The solid was slurried in dichloromethane (20 mL) and filtered to give 2-(2,4-dihydroxy-3-methylbenzoyl)benzoic acid as an off white powder (4.6 g, 16.9 mmol, 42% yield).

Step 2: Bromine (2.6 g, 16.9 mmol) was dripped into a stirring solution of the product from Step 1 (4.6 g=16.9 mmol) dissolved in acetic acid (42 mL). Monitoring by HPLC showed complete bromination within 1 hour. The solution was concentrated to give a yellow powder. Slurrying in dichloromethane followed by filtration gave the desired product as an off white powder (5 g, 14.3 mmol, 85% yield).

ii. Preparation of Compound Rh-7.

2-(5-Bromo-2,4-dihydroxybenzoyl)benzoic acid (prepared as described in is above, 1 g, 2.86 mmol) was dissolved in acetic acid (14 mL). N-hexyl-N-(3-hydroxyphenyl)phenylamine (0.77 g, 2.86 mmol) was added to the solution followed by methanesulfonic acid (8.58 mmol). The solution was stirred at reflux for 4 hours. The solution was diluted with ethyl acetate (100 mL), washed with water (2×50 mL), a pH 7 phosphate buffer (2×30 mL) and brine (2×30 mL), dried over anhydrous magnesium sulfate and concentrated to a dark purple solid. Purification by silica gel column chromatography eluted the product with 5% acetone in dichloromethane (0.75 g, 1.28 mmol, 45% yield, λmax=548 nm). The structure of the product was confirmed by 1H NMR and ES MS.

Other rhodol derivates were prepared in an analogous manner:

Rh-1: 3.08 g of 2-(5-bromo-2,4-dihydroxybenzoyl)benzoic acid and 1.69 g of 3-hydroxydiphenylamine afford 3.45 g (76% yield) of Compound Rh-1.

Rh-2: 1.5 g of 2-(5-bromo-2,4-dihydroxybenzoyl)benzoic acid and 1.0 g of N-ethyl-N-(3-hydroxyphenyl)phenylamine were reacted to afford 1.78 g (77% yield) of Compound Rh-2.

Rh-3: 418 mg of 2-(5-bromo-2,4-dihydroxybenzoyl)benzoic acid and 300 mg of N-butyl-N-(3-hydroxyphenyl)phenylamine were reacted to afford 401 mg (59% yield) of Compound Rh-3.

Rh-4: 1.0 g of 2-(5-bromo-2,4-dihydroxybenzoyl)benzoic acid and 0.83 g of N-hexyl-N-(3-hydroxyphenyl)phenylamine were reacted to afford 1.2 g (71% yield) of Compound Rh-4.

Rh-5: 413 mg of 2-(5-bromo-2,4-dihydroxybenzoyl)benzoic acid and 340 mg of N-benzyl-N-(3-hydroxyphenyl)phenylamine were reacted to afford 343 mg (59% yield) of Compound Rh-5.

Rh-6: 2-(5-Bromo-2,4-dihydroxybenzoyl)benzoic acid and N-phenyl-N-(3-hydroxyphenyl)phenylamine were reacted to afford 0.410 gms (15% yield) of Compound Rh-6 ($\lambda$max=542 nm).

Rh-9: 467 mg of 2-(5-bromo-2,4-dihydroxybenzoyl)benzoic acid and 480 mg of N-hexadecyl-N-(3-hydroxyphenyl)phenylamine were reacted to afford 435 mg (44% yield) of Compound Rh-9.

Example 3

This example describes the preparation and properties of novel rhodamine-type derivatives. General Procedure (Exemplified for Compound R-2):

A mixture of dichlorofluoran (5.55 g, 15 mmol), o-toluidine (5.2 g, 48 mmol), anhydrous zinc chloride (4.5 g) and zinc oxide (1.5 g) was stirred at 200° C. for 1.5 hours. The still-hot reaction mixture was then quenched with stirring into 8% hydrochloric acid solution (300 mL) and stirred at 90° C. for 30 minutes, then filtered. The filter cake was washed with water (100 mL), dried, and dissolved in warm methanol (100 mL). The solution was made basic by addition of a solution of concentrated ammonia solution (7 mL) in methanol (15 mL), then quenched with stirring into cold water (700 mL). The slurry was filtered, and the filter cake was washed with water (150 mL) and dried overnight under reduced pressure to give a dark purple solid (22 g). This material was triturated with hot methylene chloride (100 mL) and filtered. The filtrate was purified by column chromatography on silica gel with dichloromethane/methanol as eluant. The slightly impure resulting material was further purified by recrystallization from toluene to give pale purple prisms (2.6 g). The solids from the dichloromethane trituration were heated with refluxing toluene (25 mL), filtered hot, diluted with heptane (20 mL), cooled to 20° C., and filtered to give a further 1.2 g of pale purple prisms. The residual solids from the toluene hot filtration were taken up in refluxing xylenes (15 mL) and cooled to deposit an additional 1.0 g of pale purple solid.

Compounds R1-R5 exhibited the following properties. In most cases, solvent of crystallization was incorporated into the crystals.

| Compound | Solvent of crystallization | Melting point (capillary, ° C.) | $\lambda_{max}$ (methanol, nm) |
|---|---|---|---|
| R1 | None | 268 | 544 |
| R2 | Toluene | 170 | 526 |
| R2 | Dichloromethane | 147 | 526 |
| R3 | Dichloromethane | 117 | 526 |
| R4 | Dichloromethane | 184 | 522 |
| R5 | Toluene | 122 | 520 |

Example 4

This example describes the preparation and properties of complexed materials.

General Procedure A:
The complexing agent (1.0 or 0.5 equivalents) was combined with the color forming agent and dissolved in an appropriate blend of hot methyl ethyl ketone and cyclohexane. When successful, the complex crystallized from the hot solution as it cooled as colorless or nearly colorless crystals. The crystals were collected by suction filtration and washed with an appropriate blend of methyl ethyl ketone/cyclohexane. This wash must be carefully done to avoid the precipitation of colored materials on the surface of the crystals. Analysis by 1H NMR spectroscopy defined the composition of the complex. Integral ratios of 1:1 and 2:1 of dye to complexing agent were most commonly observed and depended both on the structure of the dye and the structure of the complexing agent.

General Procedure B:
The complexing agent (1.0 or 0.5 equivalents) and color forming agent were combined and ground with an agate mortar and pestle. The resulting intimate mixture was then slurried on the mortar in a small amount of cyclohexane and the grinding was continued. Small amounts of methyl ethyl ketone were then added to facilitate dissolution of the components into the solvent and aid crystal growth. The grinding was continued until a colorless complex was formed. Often the stronger solvent (methyl ethyl ketone) was allowed to slowly evaporate during the grinding process until a critical concentration was achieved. At this point crystallization often proceeded. Once crystallization had occurred additional cyclohexane/methyl ethyl ketone was added and the slurry of crystals was transferred either to a container for further ripening (heating and stirring) or directly collected by suction filtration. The crystals were then carefully washed with an appropriate mixture of cyclohexane/methyl ethyl ketone to avoid precipitating colored dye on the surface of the crystals. Crystals from this procedure could be used to seed crystallizations using procedure A.

| Dye | Complexing Agent | Procedure | Ratio | m.p. (DSC, ° C.) |
|---|---|---|---|---|
| Benzylfluorescein | 1,10-phenanthroline | A | 1:1 | 201 |
| Benzylfluorescein | 2,9-Dimethyl-1,10-phenanthroline | A | 1:1 | 185 |
| Benzylfluorescein | 4,4'-bipyridyl | A | 2:1 | 109 |
| Benzylfluorescein | Pyrazine | A | 1:1 | 125* |
| Benzylfluorescein | Ethylpicolinate | A | 1:1 | 138 |
| F-3 | 4,4'-bipyridyl | B | 2:1 | 191 |
| F-4 | 4,4'-bipyridyl | B | 2:1 | 215 |
| F-9 | 4,4'-bipyridyl | B | 2:1 | 165 |
| F-10 | 4,4'-bipyridyl | B | 2:1 | 198 |
| Rh-1 | 2,9-Dimethyl-1,10-phenanthroline | A | 1:2 | 244* |
| Rh-1 | 4,4'-bipyridyl | A | 1:1 | 187 |
| Rh-2 | 4,4'-bipyridyl | B | 2:1 | 210 |
| Rh-4 | 2,9-Dimethyl-1,10-phenanthroline | A | 1:1 | 109 |
| Rh-4 | 2,9-Dimethyl-1,10-phenanthroline | B | 1:1 | 108 |
| Rh-4 | 4,4'-bipyridyl | B | | 160 |
| Rh-6 | 4,4'-bipyridyl | B | 2:1 | 260 |
| Rh-8 | 4,4'-bipyridyl | A | 2:1 | 180 |
| Rh-8 | 2,9-Dimethyl-1,10-phenanthroline | A | 1:1 | 142 |
| Rh-8 | Cyclic Oxalamide | A | 1:2 | 145 |

(*indicates capillary melting point.)

Example 5

This example illustrates thermal imaging members and thermal imaging methods according to the invention. The thermal imaging members provide yellow (imaging members 5A and 5B) and magenta (imaging member 5C) colors.

The following materials were used in this example:

Topas 8007, a copolymer of ethylene and norbornene, available from Ticona, 90 Morris Avenue, Summit, N.J. 07901;

Airvol 540, a grade of poly(vinyl alcohol) available from Air Products and Chemicals, Inc., Allentown, Pa.;

Zonyl FSA, a surfactant, available from DuPont Corporation, Wilmington, Del.;

Hymicron ZK-349, a grade of zinc stearate available from Cytech Products, Inc., Eliezabethtown, Ky.;

Klebosol 30V-25, a silica dispersion available from Clariant Corporation, Muttenz, Switzerland;

Glyoxal, available from Aldrich Chemical Co., Milwaukee, Wis.;

Melinex 534, a white poly(ethylene terephthalate) film base of approximately 96 microns' thickness, available from DuPont Teijin Films U.S. Limited Partnership, 1 Discover Drive, P.O. Box 411, Hopewell, Va.

A. An image-forming layer was prepared as follows:

A compound of the present invention (0.15 g) was dispersed in a mixture comprising Topas 8007 (0.15 g of a 10% solution in methylcyclohexane) and methylcyclohexane (1.2 g), using an attriter equipped with glass beads, stirred for 18 hours at room temperature. The total solid content of the resulting dispersion was 11%.

The above dispersion was used to make the coating fluid for the dye-forming layer in proportions stated below. The coating composition thus prepared was coated onto Melinex 534 using a #18 Mayer rod, and dried. The intended coating thickness was 3.9 microns.

| Ingredient | % solids in dried film |
| --- | --- |
| Dispersion | 1.5 g |
| 10% Topas 8007/methylcyclohexane | 0.493 g |
| Methylcyclohexane | 0.15 g |

B. A barrier layer was coated onto the imaging layer by applying a 10% solution of Topas 8007 in methylcyclohexane using a #12 Mayer rod, for an intended thickness of approximately 2.6 microns.

C. A slip overcoat was coated on the barrier layer. The overcoat was prepared in proportions stated below. The overcoat coating composition applied using a #18 Mayer rod for an intended thickness of 1.6 microns.

| Ingredient | % solids in dried film |
| --- | --- |
| Glyoxal | 9.59% |
| Hymicron ZK-349 | 31.42% |
| Klebosol 30V-25 | 23.53% |
| Zonyl FSA | 3.89% |
| Airvol 540 | 31.57% |

The resulting imaging member was printed using a laboratory test-bed printer equipped with a thermal head, model KYT106-12PAN13 (Kyocera Corporation, 6 Takedatoba-dono-cho, Fushimi-ku, Kyoto, Japan).

The following printing parameters were used:

| | |
| --- | --- |
| Printhead width: | 4 inches |
| Pixels per inch: | 300 |
| Resistor size: | 70 × 80 microns |
| Resistance: | 4047 Ohm |
| Line Speed: | 7 milliseconds per line |
| Pressure: | 1.5-2 lb/linear inch |
| Dot pattern: | Rectangular grid. |

The following results were obtained from imaging members prepared using:

Imaging Member 5A: benzyl fluorescein (mp 191° C.);
Imaging Member 5B: a novel fluorescein compound of the present invention (F-11, mp 210° C.); and
Imaging Member 5C: a novel complex of the present invention prepared from the novel rhodol-type compound Rh-4 and 2,9-dimethyl-1,10-phenanthroline (mp 109° C.).

| Voltage = 14 V | | Voltage = 16 V | |
| --- | --- | --- | --- |
| Energy (J/cm$^2$) | Density (blue) | Energy (J/cm$^2$) | Density (blue) |
| Imaging Member 5A | | | |
| 4.01 | 0.07 | 5.24 | 0.51 |
| 3.61 | 0.06 | 4.72 | 0.31 |
| 3.21 | 0.04 | 4.19 | 0.15 |
| 2.81 | 0.04 | 3.67 | 0.08 |
| 2.41 | 0.04 | 3.14 | 0.07 |
| 2.01 | 0.04 | 2.62 | 0.04 |
| 1.61 | 0.04 | 2.10 | 0.04 |
| 1.20 | 0.04 | 1.57 | 0.04 |
| 0.80 | 0.04 | 1.05 | 0.04 |
| 0.40 | 0.04 | 0.52 | 0.04 |
| 0.00 | 0.04 | 0.00 | 0.04 |
| Imaging Member 5B | | | |
| 4.01 | 0.13 | 5.24 | 1.1 |
| 3.61 | 0.1 | 4.72 | 1.03 |
| 3.21 | 0.08 | 4.19 | 0.71 |
| 2.81 | 0.08 | 3.67 | 0.42 |
| 2.41 | 0.07 | 3.14 | 0.16 |
| 2.01 | 0.07 | 2.62 | 0.1 |
| 1.61 | 0.07 | 2.10 | 0.07 |
| 1.20 | 0.07 | 1.57 | 0.06 |
| 0.80 | 0.07 | 1.05 | 0.07 |
| 0.40 | 0.07 | 0.52 | 0.06 |
| 0.00 | 0.06 | 0.00 | 0.06 |

| Imaging Member 5C | | | |
| --- | --- | --- | --- |
| Voltage = 14 V | | Voltage = 16 V | |
| Energy (J/cm$^2$) | Density (green) | Energy (J/cm$^2$) | Density (green) |
| 4.01 | 0.67 | 5.24 | 0.51 |
| 3.61 | 0.48 | 4.72 | 0.48 |
| 3.21 | 0.52 | 4.19 | 0.47 |
| 2.81 | 0.42 | 3.67 | 0.47 |
| 2.41 | 0.28 | 3.14 | 0.53 |
| 2.01 | 0.19 | 2.62 | 0.34 |
| 1.61 | 0.11 | 2.10 | 0.29 |
| 1.20 | 0.1 | 1.57 | 0.17 |
| 0.80 | 0.1 | 1.05 | 0.09 |
| 0.40 | 0.09 | 0.52 | 0.08 |
| 0.00 | 0.09 | 0.00 | 0.09 |

The following conclusions may be drawn:

a. The density with no printing energy applied was, for the three imaging members, 0.04, 0.06 and 0.09, indicating that the unmelted crystalline dispersions coated to form the color-forming layer were initially substantially colorless;

b. The maximum densities achieved for the three imaging members were, respectively, 0.51, 1.1 and 0.7. As described above, the only active components in the three color-forming layers were benzyl fluorescein, F-11, and the complex formed between Rh-4 and 2,9-dimethyl-1,10-phenanthroline, respectively. No developers or other chemical adjuvants were present. Therefore, the color formed must have arisen through intrinsic color change of these materials.

c. For imaging members A and B, whose melting points were 191° C. and 210° C., respectively, imaging occurred when 16V was applied to the print head whereas very little color change was observed with 14 V applied. On the other hand, for imaging member C, with melting point 109° C., substantial color change was observed under both 16V and 14V printing conditions. The amount of energy applied during printing at 14V is lower than that applied while printing at 16V, and consequently the temperature achieved in the color-forming layer is lower for 14V printing than for 16 V printing. Whether or not color is formed can therefore be concluded to depend upon the melting point of the color-forming layer and the temperature of heating.

d. The maximum density achieved in Imaging Member A (0.51) is lower than that achieved in Imaging Member B (1.1). Imaging Member A comprises benzyl fluorescein, a known compound, whereas Imaging Member B comprises F-11, a preferred, novel, fluorescein derivative of the invention.

Example 6

This example illustrates a thermal imaging member and thermal imaging method according to the invention. The thermal imaging member provides a cyan color.

In addition to the materials described in Example 5 above, the following materials were used in this example:

Piccotac 1115, available from Eastman Chemical Company, 100 North Eastman Road, P.O. Box 511, Kingsport, Tenn.;

Melinex 6265, a white poly(ethylene terephthalate) film base of approximately 96 microns' thickness, available from DuPont Teijin Films U.S. Limited Partnership, 1 Discover Drive, P.O. Box 411, Hopewell, Va.

A. An image-forming layer was prepared as follows:

Compound R-6 of the present invention (0.08 g) was dispersed in a mixture comprising Topas 8007/Piccotac 1115 (ratio 1:1.25, 0.08 g of a 10% solution in methylcyclohexane) and methylcyclohexane (0.76 g), using an attriter equipped with glass beads, and stirred for 18 hours at room temperature. The total solid content of the resulting dispersion was 10%.

The above dispersion was used to make the coating fluid for the dye-forming layer in proportions stated below. The coating composition thus prepared was coated onto Melinex 6265 using a #9 Mayer rod, and dried. The intended coating thickness was approximately 2 microns.

| Ingredient | Amounts in coating fluid |
| --- | --- |
| Dispersion | 0.93 g |
| 10% Topas | 1.63 g |
| 8007: Piccotac 1115/methylcyclohexane | |
| Methylcyclohexane | 0.09 g |

B. A barrier layer was coated onto the imaging layer by applying a 10% solution of 1:1.25 Topas 8007/Piccotac 1115 in methylcyclohexane using a #12 Mayer rod, for an intended thickness of approximately 2.6 microns.

C. A slip overcoat was coated on the barrier layer. The overcoat was prepared in proportions stated below. The overcoat coating composition applied using a #18 Mayer rod for an intended thickness of 1.6 microns.

| Ingredient | % solids in dried film |
| --- | --- |
| Glyoxal | 9.59% |
| Hymicron ZK-349 | 31.42% |
| Klebosol 30V-25 | 23.53% |
| Zonyl FSA | 3.89% |
| Airvol 540 | 31.57% |

The resulting imaging member was printed using a laboratory test-bed printer equipped with a thermal head, model KYT106-12PAN13 (Kyocera Corporation, 6 Takedatoba-dono-cho, Fushimi-ku, Kyoto, Japan).

The following printing parameters were used:

| | |
| --- | --- |
| Printhead width: | 4 inches |
| Pixels per inch: | 300 |
| Resistor size: | 70 × 80 microns |
| Resistance: | 4291 Ohm |
| Line Speed: | 7 milliseconds per line |
| Pressure: | 1.5-2 lb/linear inch |
| Dot pattern: | Rectangular grid. |

The following results were obtained:

| Voltage = 16.5 V | |
| --- | --- |
| Energy (J/cm$^2$) | Density (red) |
| 5.88 | 1.13 |
| 5.29 | 1.10 |
| 4.71 | 1.05 |
| 4.12 | 0.79 |
| 3.53 | 0.52 |
| 2.94 | 0.30 |
| 2.35 | 0.14 |
| 1.76 | 0.1 |
| 1.18 | 0.1 |
| 0.59 | 0.1 |
| 0.00 | 0.1 |

Example 7

This example illustrates a thermal imaging member comprising more than one color-forming layer, designed to be printed with a single thermal print-head as described in above-mentioned patent application Ser. No. 10/151,432. In this example the topmost layer, printed in a relatively short time at a relatively high temperature, comprises a material of the present invention. The lower layer, printed in a relatively long time at a relatively low temperature, comprises a prior art color-forming composition in which two compounds (a leuco dye and an acid developer) that react together to form color are brought together by melting and diffusing.

In addition to materials described in Examples 5 and 6 above, the following materials were used in this Example:

Leuco dye Red 40, 3,3-bis(1-n-butyl-2-methyl-indol-3-yl) phthalide (available from Yamamoto Chemical Industry Co., Ltd., Wakayama, Japan);

Acid Developer TGSA, bis(3-allyl-4-hydroxyphenyl)sulfone, available from Nippon Kayaku Co., Ltd, Tokyo, Japan;

Airvol 205, a grade of poly(vinyl alcohol) available from Air Products and Chemicals, Inc., Allentown, Pa.;

Airvol 325, a grade of poly(vinyl alcohol) available from Air Products and Chemicals, Inc., Allentown, Pa.;

Zonyl FSN, a surfactant, available from DuPont Corporation, Wilmington, Del.;

Elvacite 2045, a grade of poly(isobutyl methacrylate), available from Lucite International Inc., 7275 Goodlett Farms Parkway, Cordova, Tenn.; Aerosol OT-100, a surfactant available from Cytec Industries, Inc., West Paterson, N.J.

A white, reflective layer was coated onto the back of a clear poly(ethylene terephthalate) substrate of 125 micron thickness (Cronar 512, available DuPont Teijin Films U.S. Limited Partnership, 1 Discover Drive, P.O. Box 411, Hopewell, Va.). The following layers were applied to the opposite side of the substrate:

A. Prior Art Color-Forming Layer, Affording a Magenta Color.

An aqueous dispersion of a magenta color-former (Red 40), poly(vinyl alcohol) (Airvol 205) and a surfactant (Zonyl FSN) was mixed with an aqueous dispersion of an acid developer (TGSA), poly(vinyl alcohol) (Airvol 205) and a surfactant (Zonyl FSN). A solution of poly(vinyl alcohol) binder (Airvol 540) in water was added and the resultant fluid was coated for a dried coverage of Red 40: 300 mg/m2, TGSA 1139 mg/m2, Zonyl FSN 13 mg/m2, and combined poly (vinyl alcohol) (Airvol 205 and Airvol 540) 661 mg/m2.

B. A Thermally-Insulating Interlayer.

A solution of Elvacite 2045 in methylcyclohexane was coated to a dried coverage of 8016 mg/m2.

C. Yellow Color-Forming Layer of the Present Invention.

A dispersion of Compound F-11 of the present invention was prepared as follows:

Compound F-11 (600 g), surfactant Aerosol OT-100 (30 g), heptanes (1.1 kg) and ethyl acetate (600 g) were combined and transferred into a 1S-Attritor containing 6.3 kg mullite beads. The jacket temperature was set to 10° C. and the attritor was run at 100 rpm for 24 hours. The grinding media was filtered off and washed with heptanes (500 g). The resulting suspension of crystalline Compound F-11 was concentrated to dryness yielding 620 g of white solid. This solid was redispersed in an aqueous solution of poly(vinyl alcohol) (Airvol 540) containing a surfactant (Zonyl FSN) to produce a coating fluid, which was coated to a dried coverage of Compound F-11: 1184 mg/m2, Aerosol OT-100: 59.2 mg/m2, Airvol 540: 344 mg/m2, and Zonyl FSN 11 mg/m2.

D. An Oxygen Barrier Layer.

The following materials were coated from aqueous solution to give the indicated dried coverages: poly(vinyl alcohol) (Airvol 325, 1454 mg/m2), boric acid crosslinker (125 mg/m2) and Zonyl FSN (32 mg/m2).

E. A UV-Absorbing Barrier Layer.

An aqueous fluid was coated to provide the following dried coverages: nanoparticulate zinc oxide (UV absorber, 2153 mg/m2), poly(vinyl alcohol) (Airvol 325, 1615 mg/m2), Zonyl FSN (32 mg/m2).

F. A Slip Coat.

An aqueous coating fluid was coated to give the following dried coverages: Hymicron ZK-349 (312 32 mg/m2), Airvol 540 (635 32 mg/m2), Klebosol 30V-25 (517 32 mg/m2) and Zonyl FSN (32 32 mg/m2).

The resulting imaging member was printed using a laboratory test-bed printer equipped with a thermal head, model KPT163 (Kyocera Corporation, 6 Takedatobadono-cho, Fushimi-ku, Kyoto, Japan).

The following printing parameters were used:

| Pixels per inch: | 300 |
|---|---|
| Resistor size: | 70 × 120 microns |
| Resistance: | 3135 Ohm |
| Line Speed: | 11.1 milliseconds per line |
| Pressure: | 1.5-2 lb/linear inch |
| Voltage: | 40.9 V |
| Dot pattern: | Rectangular grid. |

The time taken to print each line was divided into 667 equal time elements. Energy was supplied to the print head for a proportion of each of these time elements referred to as the "duty cycle". For high average power in printing, the duty cycle was a high proportion of the total duration of the time element, while for low average power the duty cycle was a low proportion of the total duration of the time element. Because of both the time taken for thermal diffusion and the large size of the resistor relative to the distance traveled by the imaging element during each time element, the thermal pulses of each of the time elements were not resolved as individual dots on the imaging element. Instead, the imaging element experienced an averaging of the power of the individual pulses.

The following results were obtained:

| High power, short time Duty cycle = 0.74 | | |
|---|---|---|
| Time elements energized (667 maximum) | Density (blue) | Density (Green) |
| 0 | 0.155 | 0.17 |
| 16 | 0.195 | 0.172 |
| 18 | 0.259 | 0.18 |
| 20 | 0.399 | 0.202 |
| 23 | 0.621 | 0.239 |
| 25 | 0.799 | 0.277 |
| 27 | 0.936 | 0.306 |
| 29 | 1.095 | 0.343 |
| 32 | 1.221 | 0.386 |
| 34 | 1.30 | 0.433 |
| 36 | 1.326 | 0.425 |

| Low power, long time Duty cycle = 0.08 | | |
|---|---|---|
| Time elements energised (667 maximum) | Density (blue) | Density (Green) |
| 0 | 0.156 | 0.173 |
| 250 | 0.187 | 0.192 |
| 292 | 0.205 | 0.225 |
| 335 | 0.226 | 0.303 |
| 377 | 0.266 | 0.467 |

-continued

Low power, long time
Duty cycle = 0.08

| Time elements energised (667 maximum) | Density (blue) | Density (Green) |
|---|---|---|
| 419 | 0.33 | 0.725 |
| 462 | 0.418 | 1.065 |
| 504 | 0.518 | 1.361 |
| 546 | 0.627 | 1.597 |
| 589 | 0.69 | 1.679 |
| 631 | 0.693 | 1.703 |

It is readily apparent that in the high power, short time printing condition the blue density exceeds the green density (i.e., the yellow color predominates over the magenta color). In the low power, long time printing condition the green density exceeds the blue density (i.e., the magenta color predominates over the yellow color). The unwanted green density observed when printing yellow is mostly due to absorption of green light by the yellow dye. Likewise, the unwanted blue density observed while printing the magenta dye is mostly due to absorption of blue light by the magenta dye. Thus, Compound F-11 of the present invention can serve efficiently as an element in a thermal imaging member comprising more than one color-forming layer, designed to be printed with a single thermal print-head as described in above-mentioned patent application Ser. No. 10/151,432.

Example 8

This example illustrates the time-independence of the color-forming temperature of a thermal imaging member according to the invention.

The color-forming layer of Imaging Member A described in Example 5 above was subjected to heating using a thermal pressure laminator/sealer available from Sencorp Equipment, Hyannis, Mass. This device allows for the independent control of the time and temperature of heating of a sample. The optical densities (blue) obtained were as follows:

| Temperature (° C.) | Time (seconds) | | | | |
|---|---|---|---|---|---|
| | 0.01 | .1 | 1 | 10 | 90 |
| 188 | .49 | .59 | .47 | — | — |
| 182 | .35 | .58 | .55 | — | .28 |
| 177 | .36 | .29 | .35 | .41 | .19 |
| 166 | .11 | .08 | .09 | .08 | .18 |
| 160 | .04 | .06 | .04 | .05 | .07 |

It can be seen that over about four orders of magnitude in heating time, color change occurred between nominal 160 and nominal 177° C.

The use of laser exposure to form an image with thermal imaging members of the present invention will now be described in more detail. The advantages of laser-activation, in comparison to heating using thermal print heads, are many. Thermal print heads must be pressed against a surface of the imaging member and maintained in sliding contact during the formation of an image. This can result in scratching and/or abrasion of the surface of the thermal imaging member and/or of the thermal print head. Moreover, if precise thermal contact is not maintained, imaging artifacts caused by uneven heating may be seen. In contrast, laser exposure does not require physical contact.

Without the requirement of physical contact, the imaging member may be transported more easily beneath the thermal source without being subject to the friction of a sliding contact, which can lead to stick/slip or "chatter" in the transport mechanism.

To support the pressure from a thermal print head, the imaging member is normally backed up by a rotating platen. Imperfections in the shape or uniformity of such a platen can affect the printing. Laser exposure does not require a rotating platen.

The heating elements in a thermal print head are fixed in a linear array such that each element executes the same motion, printing one line at a time, when the imaging member is translated relative to the thermal print head. With a laser or laser array, there is a possibility for the light output to be scanned in the printing direction, allowing the printing of multiple lines at a time, thus reducing the time to print an entire image.

A thermal print head can only introduce heat from the surface of the thermal imaging member with which it is in contact. Laser exposure allows the possibility of introducing heat internally to the structure. Additionally, the laser output may be introduced from the rear of the thermal imaging member, provided of course that the substrate is transparent to the wavelengths being used.

One method of using laser light for imaging a multi-color direct thermal imaging member is to place a light-absorbing layer at or near the surface of the member. The output from a laser incident on this layer will be absorbed and will produce localized heating. This source will function very much like the heat produced by a small electrical heater (such as is found in a thermal print head) in thermal contact with the surface of the medium.

Another method of using laser light is to include an absorber of laser radiation at or near each individual color-forming layer buried within the thermal imaging member, and to irradiate with a laser only long enough to activate that particular color-forming layer and no others. This method may require the use of three non-visible laser wavelengths, and three absorbers matched to these wavelengths. Alternatively, the focusing plane of a single wavelength laser (with optics arranged to have a shallow depth of field) may be varied to selectively heat one of the three absorbers buried at different depths of the imaging member. Of course, none of the absorbers should absorb in the visible region of the spectrum, as such absorption would be visibly colored and would interfere with the viewing of the colored image. As noted above, it is preferred in the practice of the present invention that the laser emit in the near infra-red (NIR) region of the electromagnetic spectrum.

Suitable radiation-absorbing materials for NIR radiation are well known in the art, and include (but are not limited to) dye materials such as cyanines, hemicyanines, squaraines and squaryliums, croconiums, porphyrins, phthalocyanines, organo-nickel and organo-platinum compounds, and inorganic materials such as metal oxides, carbon black, and the like. Suitable radiation-absorbing compounds that are known in the art can be found in "Infrared Absorbing Dyes", Matsuoka, Masaru, ed., Plenum Press, New York, 1990 and "Near-Infrared Dyes for High Technology Applications", Daehne, Resch-Genger, Wolfbeis, Kluwer Academic Publishers, as well as the above-referenced U.S. Pat. Nos. 5,227,498, 5,227,499, 5,231,190, 5,262,549, 5,354,873, 5,405,976, 5,627,014, 5,656,750, 5,795,981, 5,919,950, 5,977,351 and 6,482,950. When longer IR wavelengths are used, such as are available from gas lasers such as $CO_2$ lasers, suitable absorbers include silicate materials such as clays, for example, Montmorillonite, Bentonite, Laponite and similar materials For the more practical situation in which a single, non-visible laser wavelength is used, a single absorbing layer can be placed on the surface of a multicolor thermal imaging member of the type described in U.S. Pat. No. 6,801,233, or one or more absorbing layers may be disposed internally to the structure. Laser irradiation of these absorbing layer(s) can provide the heat to activate color-forming layers. By appropriate choices of laser pulse power and pulse length, the time and temperature of heating of color-forming layers can be controlled so that at least partially independent addressing of color-forming layers can be achieved, as described in detail in U.S. Pat. No. 6,801,233.

In a preferred embodiment of the present invention, the thermal imaging member comprises three color-forming layers, each of which afford one of the subtractive primary colors (i.e., yellow, magenta, and cyan). Other, optional color-forming layers might also be provided, giving rise to colors such as black, etc., as will be apparent to one of ordinary skill in the imaging art. Separating the three color-forming layers are two thermally-insulating interlayers whose properties are described in detail in copending U.S. patent application Ser. No. 12/462,421. Additional layers may be included inside or outside of this combination for purposes such as protection from ultraviolet, oxygen and water, mechanical support, etc., as are well known in the art.

The three color-forming layers have different activation temperatures. The color-forming layer with the highest activation temperature is hereinafter referred to as the "T-high layer", the layer with the intermediate activation temperature as the "T-medium" layer, and the layer with the lowest activation temperature as the "T-low" layer. The colors provided by these color-forming layers are, as noted above, preferably yellow, magenta and cyan, although there is no requirement that a particular activation temperature be associated with a particular color.

The symbol "IL" is used hereinafter to represent a thermally-insulating interlayer separating two color-forming layers.

Figure 4:
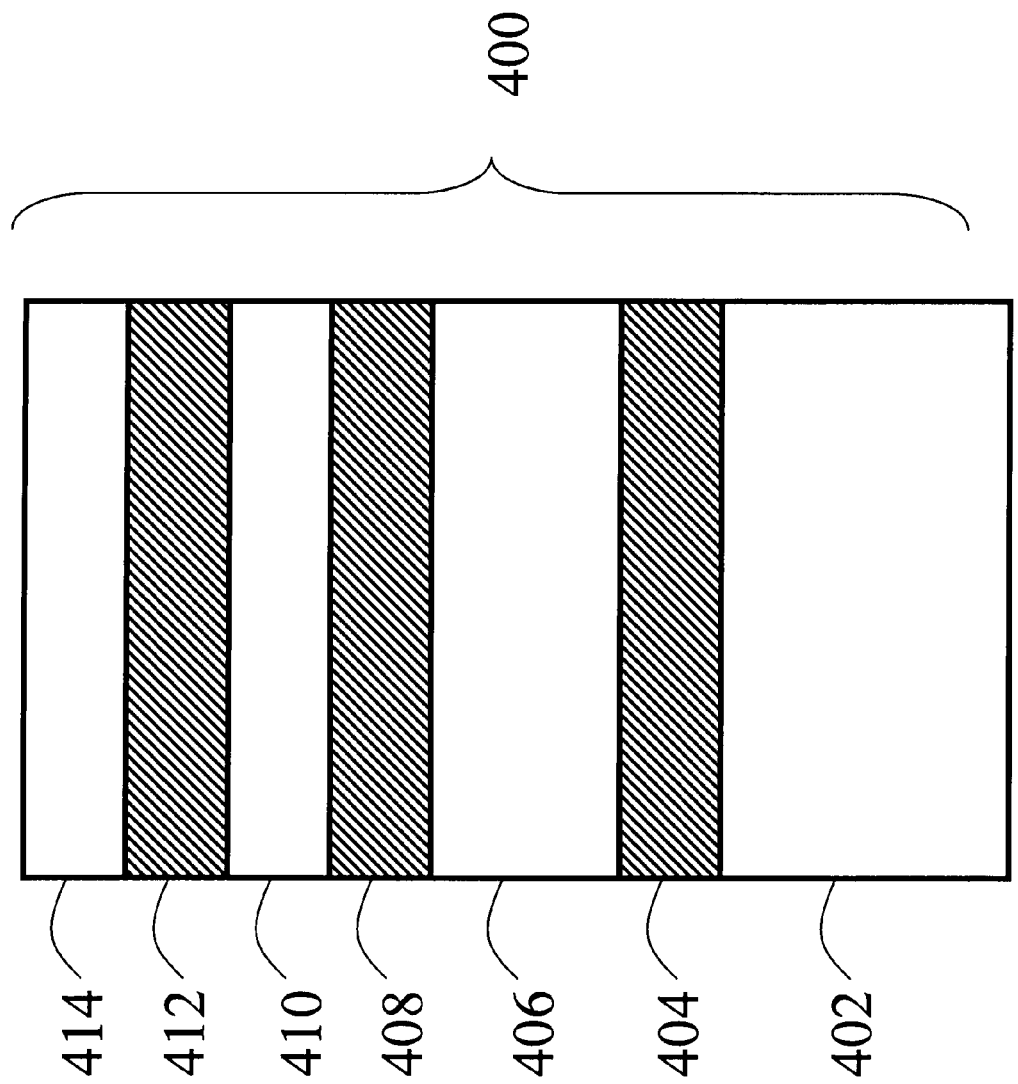
FIG. 4 illustrates a thermal imaging member of the invention.

Referring now to FIG. 4, there is seen a preferred thermal imaging member 400 of the invention.

Substrate 402 can be opaque or transparent, a flexible web or a stiff material such as a card or an optical disc. Substrate 402 may be composed of paper, plastic, metal or other materials that will occur to those of ordinary skill in the art. Substrate 402 bears three color-forming layers 404, 408 and 412, two thermally-insulating layers 406 and 410 that are preferably not of the same thickness, and an optional protective layer 414.

The activating temperatures selected for the color-forming layers are generally in the range of about 90° C. to about 300° C. The activating temperature T-low layer is preferably as low as possible consistent with thermal stability of the imaging member during shipment and storage and preferably is about 90° C. or more. The activating temperature of the T-high color-forming layer is preferably as low as possible consistent with allowing the activation of the T-medium and T-low color-forming layers when incident laser irradiation is absorbed according to the invention, and preferably is about 200° C. or more. The activating temperature of the T-medium color-forming layer is between that of the T-low and T-high layers and is preferably between about 140° C. and about 180° C.

In one embodiment of the present invention, the color-forming layers comprise a material that is colorless in the crystalline form and colored in an amorphous form as described in detail above. The T-high layer preferably comprises no other fusible material except the crystalline color-forming material, since it is important that in this layer the activation temperature be as independent of the heating time as possible.

One or more thermal solvents, which are crystalline, fusible materials, may be incorporated into the color-forming layers in certain preferred embodiments of the thermal imaging member. The crystalline thermal solvent(s), upon being heated, melt and thereafter dissolve or liquefy the crystalline color-forming material, thereby converting it to an amorphous form and providing a color change (i.e., an image). Thermal solvents may be advantageously used when it is required for a color-forming layer to have an activation temperature that is lower than the melting point of the crystalline color-forming material itself. The melting point of the thermal solvent, rather than that of the crystalline color-forming material, may in such a case establish the activation temperature of the color-forming layer.

It will be clear to one of ordinary skill in the art that the activation temperature of a color-forming layer that comprises a mixture of crystalline materials may be different from the melting points of any of the individual components. A eutectic mixture of two crystalline components, for example, melts at a lower temperature than either of the components in isolation. Conversely, if the rate of solubilization of the crystalline color-forming material in the molten thermal solvent is slow, the activation temperature of the mixture may be higher than the melting point of the thermal solvent. Recall that the activation temperature of a mixture of a crystalline color-forming material and a thermal solvent is the temperature at which the color of the mixture changes, i.e., the temperature at which a sufficient amount of the crystalline color-forming material dissolves in the molten thermal solvent to provide a visible color change. It will be clear from the above discussion that the activation temperature of a mixture of a crystalline color-forming material and a thermal solvent or solvents may be dependent upon the rate of heating. In the design of thermal imaging members of the present invention, therefore, determination of the actual activation temperature of a composition is preferred to be carried out experimentally.

Any suitable thermal solvent may be incorporated into the color-forming layers of the thermal imaging members of the invention. Suitable thermal solvents include, for example, aromatic and aliphatic ethers, diethers and polyethers, alkanols containing at least about 12 carbon atoms, alkanediols containing at least about 12 carbon atoms, monocarboxylic acids containing at least about 12 carbon atoms, esters and amides of such acids, aryl amides, especially benzanilides, aryl sulfonamides and hydroxyalkyl-substituted arenes.

Specific preferred thermal solvents include: 1,2-diphenoxyethane, 1,2-bis(4-methylphenoxy)ethane, tetradecan-1-ol, hexadecan-1-ol, octadecan-1-ol, dodecane-1,2-diol, hexadecane-1,16-diol, myristic acid, palmitic acid, stearic acid, methyl docosanoate, 1,4-bis(hydroxymethyl)benzene, diaryl sulfones such as diphenylsulfone, 4,4'-dimethyldiphenylsulfone, phenyl p-tolylsulfone and 4,4'-dichlorodiphenylsulfone, and p-toluenesulfonamide.

Particularly preferred thermal solvents are ethers such as 1,2-bis(2,4-dimethylphenoxy)ethane, 1,4-bis(4-methylphenoxymethyl)benzene, bis(4-phenoxyphenoxymethyl)benzene and 1,4-bis(benzyloxy)benzene.

It is possible that the dissolution of the crystalline color-forming material by a thermal solvent may lead to an amorphous form in which the amount of color that is formed is different from the amount that would be present in an amorphous form resulting from melting the crystalline color-forming material alone (i.e., without interaction with the thermal solvent). Typically, the crystalline color-forming materials of the present invention are tautomeric compounds in which at least one tautomer is colorless and at least another tautomer is colored. The crystalline form comprises substantially the colorless tautomer, whereas the colored form comprises both tautomers in proportions that depend upon the structure of the particular color-forming material and the environment in which it is located. The proportion of the colored tautomer in the amorphous material may be enhanced by use of hydrogen-bonding or acidic adjuvants. It is possible that such materials may actually protonate the color-forming material to produce a new, colored compound. Materials that increase the proportion of the color-forming material that is in a colored form are hereinafter referred to as "developers". It is possible that the same compound may serve the function of thermal solvent and developer. Preferred developers include phenols such as 4,4'-butylidenebis[2-(1,1-dimethylethyl)-5-methyl-phenol], 2,2'-methylenebis(6-tert-butyl-4-methylphenol), 2,2'-methylenebis(6-tert-butyl-4-ethylphenol), 2,2'-ethylidenebis(4,6-di-tert-butylphenol), bis[2-hydroxy-5-methyl-3-(1-methylcyclohexyl)phenyl]methane, 1,3,5-tris(2,6-dimethyl-3-hydroxy-4-tert-butylbenzyl) isocyanurate, 2,6-bis[[3-(1,1-dimethylethyl)-2-hydroxy-5-methylphenyl]methyl]-4-methylphenol, 2,2'-butylidenebis[6-(1,1-dimethylethyl)-4-methylphenol, 2,2'-(3,5,5-trimethylhexylidene)bis[4,6-dimethyl-phenol], 2,2'-methylenebis[4,6-bis(1,1-dimethylethyl)-phenol, 2,2'-(2-methylpropylidene)bis[4,6-dimethyl-phenol], 1,1,3-tris(2-methyl-4-hydroxy-5-t-butylphenyl)butane, tris(3,5-di-t-butyl-4-hydroxybenzyl) isocyanurate, 2,2'-thiobis(4-tert-octylphenol), and 3-tert-butyl-4-hydroxy-5-methylphenyl sulfide.

In order for the image formed by the amorphous color-former to be stable against recrystallization back to the crystalline form, preferably the glass transition temperature (Tg) of the amorphous mixture of the color-former and any thermal solvent and/or developer should be higher than any temperature that the final image must survive. Typically, it is preferred that the Tg of the amorphous, colored material be at least about 50° C., and ideally above about 60° C. In order to ensure that the Tg is sufficiently high for a stable image to be formed, additional materials having a high Tg may be added to the color-forming composition. Such materials, hereinafter referred to as "stabilizers", when dissolved in the amorphous mixture of color-former, optional thermal solvent, and optional developer, serve to increase the thermal stability of the image.

Preferred stabilizers have a Tg that is at least about 60° C., and preferably above about 80° C. Examples of such stabilizers are the aforementioned 1,3,5-tris(2,6-dimethyl-3-hydroxy-4-tert-butylbenzyl) isocyanurate (Tg 123° C.) and 1,1, 3-tris(2-methyl-4-hydroxy-5-t-butylphenyl)butane (Tg 101° C.). The stabilizer molecule may also serve as a thermal solvent or as a developer.

For example, the color-forming material may itself have a melting temperature above the desired temperature for imaging, and a Tg (in the amorphous form) of about 60° C. In order to produce a color-forming composition melting at the desired temperature, it may be combined with a thermal solvent that melts at the desired temperature for imaging. The combination of thermal solvent and color-forming material may, however, have a Tg that is substantially lower than 60° C., rendering the (amorphous) image unstable. In this case, a stabilizer such as 1,3,5-tris(2,6-dimethyl-3-hydroxy-4-tert-butylbenzyl) isocyanurate may be added, to raise the Tg of the amorphous material. In addition, there may be provided a developer, for example, a phenolic compound such as 2,2'-ethylidenebis(4,6-di-tert-butylphenol), in order to increase the proportion of the color-forming material that is in the colored form in the amorphous phase.

Preferably the color-forming compound of the present invention, the (optional) thermal solvent, the (optional) developer and the (optional) stabilizer are each predominantly in their crystalline forms prior to imaging. By "predominantly" is meant at least about 50% and preferably more than that. During imaging, at least one of these materials melts and an amorphous mixture of the materials is formed. As noted above, the amorphous mixture is colored, whereas the crystalline starting materials are colorless.

The temperature range over which melting (and therefore coloration) occurs should be as narrow as possible, especially in the case that the crystalline color-forming compounds are incorporated into a thermal imaging member capable of forming full-color images. It is preferred that the temperature range of melting (as measured by differential scanning calorimetry) of a color-forming composition comprising a crystalline color-forming compound be less than 15° C. as measured at the half height of the peak, and preferably less than 10° C. measured at half height.

It is possible that one of the components in the amorphous, colored mixture may recrystallize after the image has been formed. It is desirable that such recrystallization not change the color of the image. In the case that a color-former, thermal solvent, developer and stabilizer are used, the thermal solvent may typically recrystallize without greatly affecting the color of the image.

Color-forming layers may comprise any of the image-forming materials described above, or any other thermally-activated colorants, and are typically from about 0.5 to about 4.0 µm in thickness. Color-forming layers may also comprise more than one layer (hereinafter referred to as "sub-layers"), which may not have identical composition. For example, a crystalline color-forming material may be incorporated into one sub-layer while a thermal solvent may be located in another. Other arrangements, including sub-layers for control of the rates of chemical diffusion, will occur to those of ordinary skill in the art. In such cases each of the constituent sub-layers is typically from about 0.1 to about 3.0 µm in thickness.

Color-forming layers may comprise dispersions of solid materials, encapsulated liquid, amorphous or solid materials or solutions of active materials in polymeric binders, or any combinations of the above.

Preferred binder materials for use in color-forming layers include water-soluble polymers such as poly(vinyl alcohol), ethylene vinyl alcohol polymers, polyacrylamide, gelatin, cellulosic materials, and salts of carboxylated polymers (for example, ammonium salts of polymers containing acrylic acid units).

In addition, other layers (not shown) may be present, for example to protect the image from light, humidity, oxygen, etc., or to promote physical properties such as adhesion, as is well known in the art.

Although in FIG. 4, thermally-insulating layer 406 is shown as thicker than thermally-insulating layer 410, this is not a requirement of the present invention. In general, a thermally-insulating layer separating a T-low from a T-medium layer is preferred to be thicker than a thermally insulating layer separating a T-medium layer from a T-high layer. Preferably, the thermally-insulating layers differ in thickness by at least a factor of two.

As described in detail in copending U.S. patent application Ser. No. 12/462,421, it is the thermal diffusivity of the thermally-insulating layers that controls the timing of the heating of the color-forming layers.

With the layer naming convention just described, there are six different orderings of the activation temperatures of the color-forming layers 404, 408 and 412. Counting from the substrate 402 in the direction of the protective layer 414, (i.e., in the order 404/406/408/410/412) they are:

a. T-high/IL/T-medium/IL/T-low;
b. T-high/IL/T-low/IL/T-medium;
c. T-medium/IL/T-high/IL/T-low;
d. T-medium/IL/T-low/IL/T-high;
e. T-low/IL/T-high/IL/T-medium; and
f. T-low/IL/T-medium/IL/T-high.

As the color-forming composition in the T-high layer has the highest activation temperature, it will normally be the case that the absorber for incident laser radiation will be either in or closely adjacent to the T-high layer. In this preferred embodiment, the other two color-forming layers are heated indirectly, in that they are activated by heat that has diffused from the vicinity of the T-high layer.

This being the case, it will be clear to one of ordinary skill in the art that it would be difficult to make a system work if the T-low layer were located between the T-high layer and the T-medium layer, as heat diffusing from T-high to T-medium and activating T-medium would also activate T-low. Consequently, two of the six orderings listed above are impractical. The workable combinations are:

1. T-high/IL/T-medium/IL/T-low;
2. T-medium/IL/T-high/IL/T-low;
3. T-low/IL/T-medium/IL/T-high; and
4. T-low/IL/T-high/IL/T-medium.

In the first and third combination, the layer stack is heated at the T-high layer (on the bottom or top, respectively) and the heat diffuses from layer to layer in succession. In the second and fourth combinations, the heating is at the central color-forming layer and diffuses simultaneously in both directions to the other color-forming layers.

In the above discussion it is assumed that there is only one layer of each activation temperature. It is also possible, however, that more than one layer may form the same color at the same temperature. For example, the more complex structure: T-low/IL/T-medium/IL/T-high*/IL/T-medium/T-low might be employed (where the asterisk denotes the presence of the absorber for laser radiation), and many other such structures will occur to those of ordinary skill in the art.

A further consideration in the ordering of layers is the presence of other surfaces. The surface of the medium through which the image is viewed (hereinafter referred to as the "top" surface of the color-forming composite, wherein the color-forming composite refers to the combination of at least layers 404, 406, 408, 410, 412 and 414 of FIG. 4) is generally an interface between the coating and air. In the case of laser activation, there may be no object in contact with this surface, and cooling of this surface will then be weak. The lower surface of the color-forming composite, though, is often in contact with some kind of support structure (e.g. supporting substrate 402 on which the active layers are coated, or some physical object to which coating layers have been applied.) This surface (hereinafter referred to as the "bottom" surface of the color-forming composite) would be subject to more cooling during printing, either by natural diffusion of heat into the support, or by any additional means provided to assist cooling.

The T-low layer, which is usually the furthest from the heat source, becomes more difficult to heat if it is adjacent to a good conductor of heat. Therefore, in a preferred embodiment of the present invention intended for laser exposure, the T-low layer is closer to the top surface of the color-forming composite than the T-medium or T-high layers. This criterion favors the use of structures #1 or #2 above. It is also preferred that the substrate 402 or support in contact with the bottom of the color-forming composite be chosen to be relatively thermally conductive, to minimize heat accumulation near the T-high or T-medium layers.

Laser irradiation may be incident from either the front or the back of the color-forming composite, provided that the materials between the laser entry point and the absorbing layer are reasonably transparent to laser light of the wavelength being used.

Even though the T-low layer has the lowest activation temperature, it is also usually the furthest from the heated layer and may be difficult to heat sufficiently in the time available for printing each pixel. It is therefore preferred in certain embodiments of the present invention to preheat the medium, particularly when higher speed printing is desired. As discussed in detail in U.S. Pat. No. 7,408,563, such preheating has the most significant effect on the T-low layer, as it can bring the "baseline temperature" of this layer close to its activation temperature and greatly reduce the amount of additional heat needed to accomplish color formation.

In one embodiment of the invention, a radiation-absorbing material is locating in a layer proximate to the T-low layer or in the T-low layer itself, and pre-heating is accomplished by irradiating the thermal imaging member with a wavelength that is absorbed by this radiation-absorbing material. The radiation-absorbing material can be chosen from the materials known in the art, as discussed above, and may be chosen absorb at a wavelength that is the same or different from that used to form the image with a laser.

Preheating of the thermal imaging member (particularly in the vicinity of the T-low layer) may be accomplished by a number of means, such as use of a heated platen, residual absorption of the laser light by the substrate or coatings on the substrate, or use of heating by another laser or source of light at the same or a different wavelength than that used to form the image.

Although preheating in the vicinity of the T-low layer can be beneficial, the same is not usually true of preheating around the T-medium or T-high layers. In the latter cases, the heating is not as significant a fraction of the total heat needed to fully activate the layer, but it is influential in determining whether the energy used to write on the T-low layer can activate any color in the T-medium or T-high layers.

The term "thermal history control", as applied to thermal printing methods, has in the past referred to measures taken to compensate for the varying temperature of the thermal print head as it prints. This type of control will be required for laser printing as well, if the power output or spectrum of the laser changes with its temperature. However, a more significant thermal history control issue in the practice of the present invention is the accumulation of heat within the thermal imaging member itself.

A thermal history control algorithm to compensate for accumulation of heat within a thermal imaging member is described in copending, commonly-assigned U.S. patent application Ser. No. 12/468,413. Therein are described methods by which sequential heat pulses applied to a thermal printing medium for the purpose of multi-color printing may be combined to produce a correction for each additional heat pulse. The correction accounts for heat carried over from each pulse to future pulses, either within the same pixel or within the next pixel printed by the same heating element. In the case of laser printing on a multicolor thermal imaging member wherein diffusion of heat is used to select which color is printed, the surface of the medium will be poorly cooled by air. Consequently, the principal cooling will usually be from diffusion of heat further into the body of the coating and the substrate, and/or from cooling by any platen or substrate that is provided as backing. As these forms of cooling are normally less effective than the cooling provided by a thermal print head, it is more important in the case of laser printing that the accumulation of heat in the structure of the thermal imaging member be accurately compensated.

In order to produce a multi-color image on a thermal imaging member of the present invention with laser exposure, it is necessary to cause the laser to "visit" each pixel location of the medium, and to deliver a series of heat pulses defined to activate selected amounts of each of the dyes. As described U.S. patent application Ser. No. 12/022,955, filed on Jan. 30, 2008, this exposure interval may consist of a set of time segments during which the three individual dye layers are printed. The exposures normally consist of:
1) a short segment, in which a relatively high average power activates the T-high layer;
2) a segment of intermediate length, in which a thermal exposure of intermediate average power activates the T-medium layer; and
3) a relatively long segment during which an exposure of low power activates the T-low layer.

Figure 5:
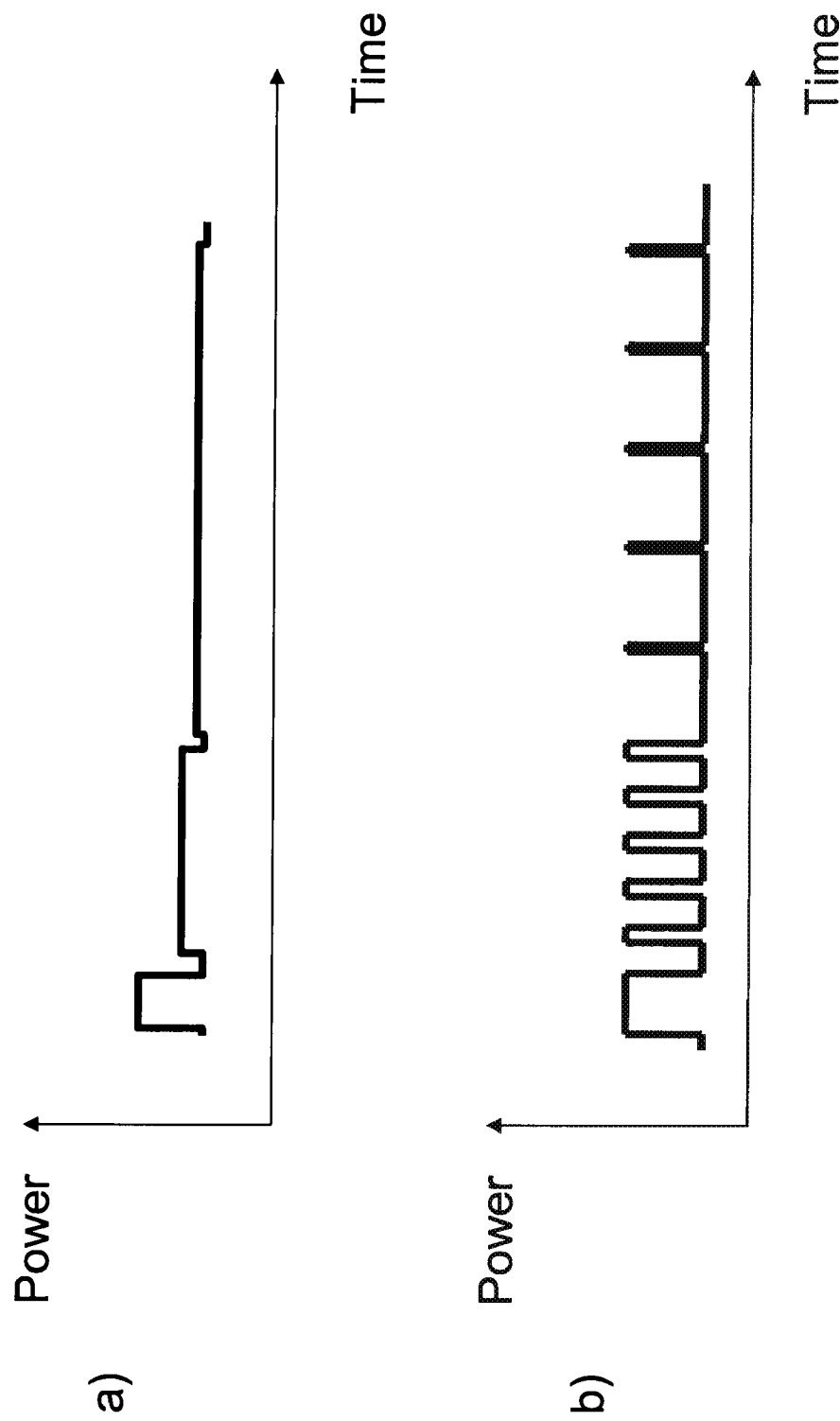
FIGS. 5 and 6 illustrate heat pulsing methods for exposing thermal imaging members of the present invention.

As in the case of a thermal print head, the power may be varied by a number of modulation methods, two of which are shown in FIG. 5. FIG. 5a illustrates a method in which the average power in each of three intervals is changed by varying the current to the laser, or by interposing a modulating device that varies the intensity of the laser beam. FIG. 5b illustrates a method in which the laser provides short pulses of full power and the average power is adjusted by varying the duty-cycle of the pulses (i.e., the ratio of on-time to total time).

Figure 6:
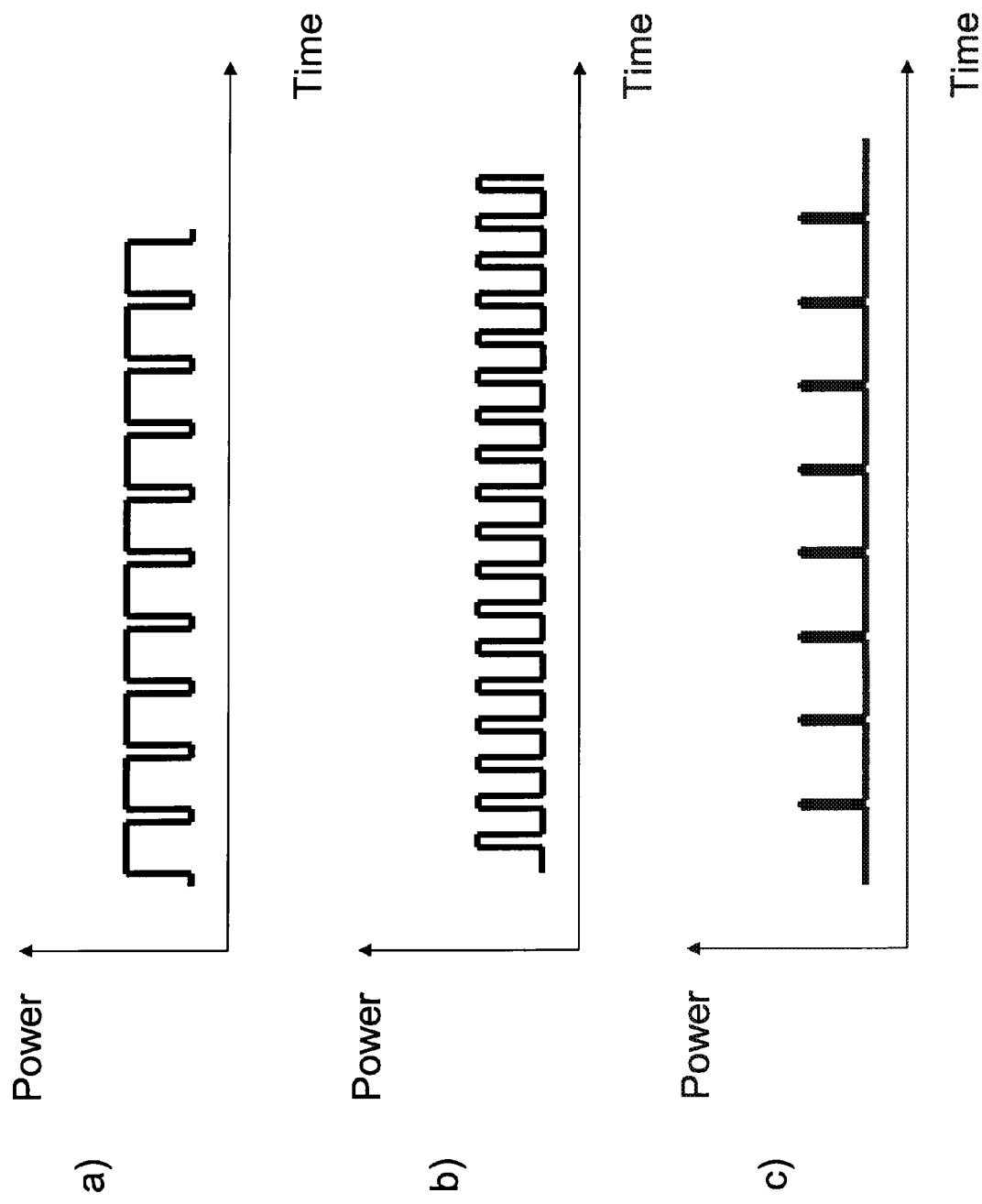

As an alternative to carrying out the full pulse sequence of FIG. 5 at each pixel before going on to the next (a process herein referred to as single-pixel successive scanning), it is possible to carry out multi-pass printing as illustrated in FIG. 6. For example, in a first pass the laser may be set to a high power and may be used to print multiple pixels in the T-high layer, up to the entire image (FIG. 6a). A second scan would use the laser at lower power and longer exposure time to print the T-medium image in multiple pixels (FIG. 6b). Finally, a pass at low power and long exposure time would produce the T-low image contents in multiple pixels (FIG. 6c). The process illustrated in FIG. 6 is herein referred to as multiple-pixel successive scanning.

The advantage of multiple-pixel successive scanning over the single-pixel version is that there may be time for heat to diffuse away from the color-forming layers before a particular pixel is addressed again, allowing the thermal history compensation to be more straightforward and, potentially, the color gamut attainable to be greater because of decreased "cross-talk" between the color-forming layers.

It is obviously necessary to employ methods for directing laser exposure to every point in a desired image. This can be accomplished in many ways, including transporting the imaging member beneath the device that is providing the laser exposure, transporting the laser with respect to the imaging member, using mirrors, prisms, or other optical devices to deflect one or more laser beams dynamically so that they scan from point to point on the imaging member, dividing a laser beam into multiple beams and redirecting each one to a different point on the medium, or using an array of lasers, each providing exposure to a different point on the medium.

It is anticipated that more than one of these methods may be combined to result in a complete exposure of the medium. For example, a relatively slow transport of the medium may be used to transport the medium in one direction past a device that performs a laser exposure along a perpendicular direction. This is analogous to a thermal print head which writes a line at a time on media that is moving perpendicular to the linear array of heaters on the thermal print head.

The scanning of laser light may be accomplished with vibrating mirrors, spinning reflectors or prisms, or other devices known in the art. At each location, the heat pulses may be modulated either by modulating the power source(s) of the laser(s), or by inserting one or more modulating devices into the path of the laser light.

One method of scanning the laser would be to use a single laser spot, and to move it in a raster pattern. It would move first from pixel to pixel in succession along a row, and then retrace to the beginning of the next row. In this type of scanning, the spot must reside at the location of each pixel for the time necessary to write all three colors, in a single-pixel successive scanning mode, or one of the individual colors in a multiple-pixel successive scanning mode. Because of the thermal diffusion process used to discriminate colors in the method of the present invention, the pixel printing time is on the order of 10 milliseconds. With typical pixel resolutions of 300 pixels per inch along a line, the writing speed is limited to about 3 seconds per linear inch of line. For a 4×6 inch print, each line would then take more than 12 seconds to print all three colors, and the entire print would take 12 seconds×1800 lines=21,600 seconds=36 minutes. This is unacceptably long for most applications.

Most practical methods of writing on thermal imaging members of the present invention therefore involve the simultaneous printing of multiple pixels. Recently, arrays of solid state IR-emitting lasers have become available, opening the possibility of printing one line of an image at a time with a linear array of lasers. As described above, an IR absorber is incorporated into the thermal imaging member to absorb the laser light and produce heat. Employed in this way, solid state laser arrays are similar to thermal print heads, in that they provide linear arrays of individually controllable energy sources with spacing adequate for imaging. The array is placed in proximity to the thermal imaging member, or is optically projected onto the member, and thereby prints in a line-at-a-time fashion. For thermal print heads and laser print heads that deliver the same energy to the pixel, the print times and modulation requirements are comparable.

Prints may be made in one, two or three passes. Independent of the number of passes, each pixel of the medium must be exposed to a short pulse of high temperature, a medium length pulse of medium temperature, and a long pulse of low temperature in order to print the three colors. In three pass printing, the short, high-temperature pulses may be provided in the first pass; the medium length, medium-temperature pulses in a second pass; and the long, low-temperature pulses in a third pass. In single pass printing, the three pulses may be applied in succession at each line before proceeding to the next line.

An array of optical sources may also be achieved by using optical elements to divide a single laser beam into an array of individual beams, and using a separate modulator for each subdivided beam.

Although the invention has been described in detail with respect to various preferred embodiments thereof, it will be recognized by those skilled in the art that the invention is not limited thereto but rather that variations and modifications can be made therein which are within the spirit of the invention and the scope of the amended claims.

What is claimed is:

1. A thermal imaging member comprising:
a substrate having first and second opposed surfaces, said first surface bearing at least a first color-forming layer, a first thermally-insulating interlayer, a second color-forming layer, a second thermally-insulating layer, and a third color-forming layer, wherein said first color-forming layer has a higher activation temperature than said second color-forming layer, and said second color-forming layer has a higher activation temperature than said third color-forming layer, said thermal imaging member further consisting of a radiation-absorbing material that is located either within said first color-forming layer or in a layer that is closer to said first color-forming layer than to any other color-forming layer;
wherein said second and third color-forming layers do not contain radiation-absorbing material;
wherein at least one of said color-forming layers comprises a chemical compound in a crystalline form, said crystalline form being capable of being converted to an amorphous form, said chemical compound having intrinsically a different color in said crystalline form than in said amorphous form.

2. The thermal imaging member of claim 1 wherein said radiation-absorbing material absorbs radiation having wavelengths in the range of 700-1200 nm.

3. The thermal imaging member of claim 2 wherein said radiation-absorbing material absorbs at least 5% of incident radiation at a wavelength that is in the range of 700-1200 nm.

4. The thermal imaging member of claim 1 wherein said second color-forming layer is not located between said first and third color-forming layers.

5. The thermal imaging member of claim 1 wherein said first color-forming layer is located at a greater distance from said first surface of said substrate than said second and said third color-forming layers.

6. The thermal imaging member of claim 1 wherein said first and second thermally-insulating layers differ in thickness by at least a factor of two.

* * * * *